(12) United States Patent
Targosz

(10) Patent No.: US 8,054,065 B2
(45) Date of Patent: Nov. 8, 2011

(54) INSPECTION OF MIXED MATERIAL DURING INSTALLATION

(76) Inventor: Thomas C. Targosz, New Baltimore, MI (US)

( * ) Notice: Subject to any disclaimer, the term of this patent is extended or adjusted under 35 U.S.C. 154(b) by 0 days.

(21) Appl. No.: 13/033,182

(22) Filed: Feb. 23, 2011

(65) Prior Publication Data

US 2011/0140889 A1   Jun. 16, 2011

Related U.S. Application Data

(60) Division of application No. 11/935,605, filed on Nov. 6, 2007, now Pat. No. 7,923,992, which is a continuation-in-part of application No. 10/808,750, filed on Mar. 25, 2004, now Pat. No. 7,148,678, and a continuation-in-part of application No. 11/608,979, filed on Dec. 11, 2006, now Pat. No. 7,327,136.

(60) Provisional application No. 60/864,422, filed on Nov. 6, 2006, provisional application No. 60/864,479, filed on Nov. 6, 2006, provisional application No. 60/870,984, filed on Dec. 20, 2006, provisional application No. 60/946,447, filed on Jun. 27, 2007, provisional application No. 60/975,550, filed on Sep. 27, 2007.

(51) Int. Cl.
*G01N 27/74* (2006.01)
*G01R 33/12* (2006.01)

(52) U.S. Cl. ............... 324/204; 73/61.42; 73/53.07
(58) Field of Classification Search ............ 324/204; 73/61.42, 53.07
See application file for complete search history.

(56) References Cited

U.S. PATENT DOCUMENTS

| 4,686,469 | A | | 8/1987 | Lewis |
| 4,816,758 | A | | 3/1989 | Theissen et al. |
| 5,315,243 | A | | 5/1994 | Kempster et al. |
| 5,831,151 | A | * | 11/1998 | Ondrus et al. ............ 73/61.41 |
| 6,560,544 | B1 | | 5/2003 | Ondrus |
| 7,148,678 | B1 | * | 12/2006 | Targosz ............ 324/204 |

* cited by examiner

*Primary Examiner* — Reena Aurora
(74) *Attorney, Agent, or Firm* — Fraser Clemens Martin & Miller LLC; William J. Clemens

(57) ABSTRACT

An apparatus and a method for monitoring a ratio of at least two components being mixed use sensors detecting ferrous taggant particles in the component(s) and the mixture. The sensors include an annular drive coil positioned between inner and outer annular sense coils all surrounding a passage for material being sensed. The ratio is determined by comparing a signal generated by one sensor through which a taggant particle containing component is flowing with a signal generated by another sensor through which the mixture is flowing delayed by the time required for the component to flow from the one sensor to the another sensor. The signals can also be used to control the flow of the components and to check the mixture after use for such mixtures as asphalt and concrete.

19 Claims, 28 Drawing Sheets

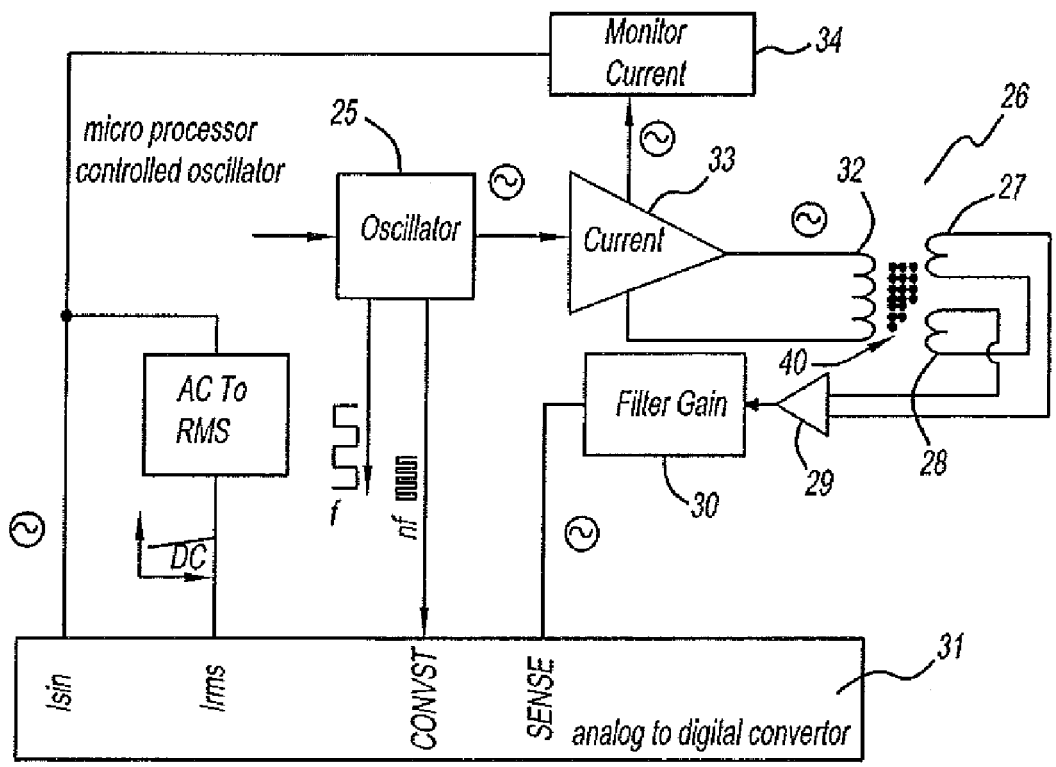
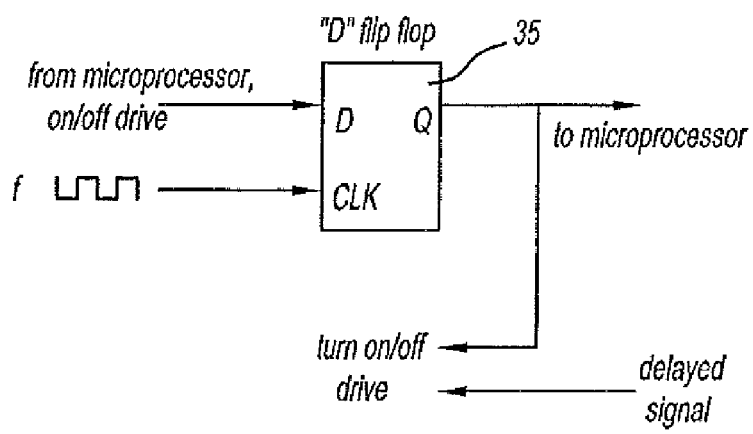
FIG-3

$V(out) = Vpk \times \sin(ph + 2 \times pi \times f \times t) + dc$

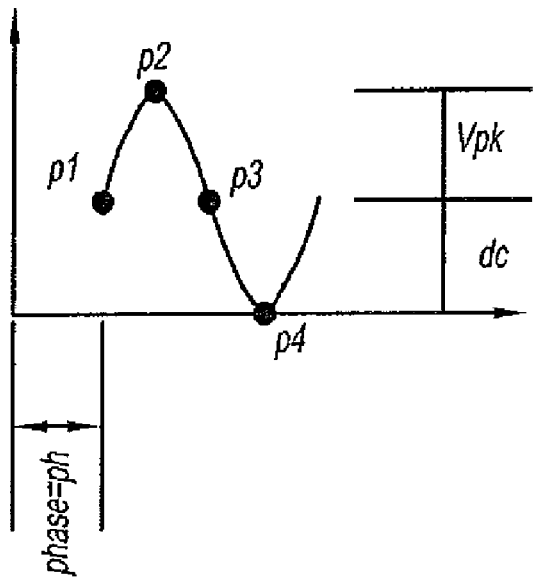

$p1 = Vpk \times \sin(phase) + dc$
$p2 = vpk \times \sin(phase + 90) + dc = Vpk \times \cos(phase) + dc$
$p3 = Vpk \times \sin(phase + 180) + dc + -Vpk \times \sin(phase) + dc$
$p4 = Vpk \times \sin(phase + 270) + dc = -Vpk \times \cos(phase) + dc$ $p1 - p3 = 2 \times Vpk \times \sin(phase)$
$p2 - p4 = 2 \times Vpk \times \cos(phase)$ $phase = \operatorname{atan}(p1 - p3)/(p2 - p4)$
$Vpk = (p1 - p3)/\sin(phase)$

FIG - 4

Footprint = 3.14159 * Diameter/2 * Height (Cubic inches Or Cubic Centimeters)

| 100% Master | Blue | Master profile, 2% of the final volume is a tagged material. |
|---|---|---|
| 50% Master | Red | Min Master profile, 1% of the final volume is a tagged material. |
| Stone + asphalt + sand + tagged material | Yellow | A profile of a well mixed specimen. This can be used as a baseline for comparing additional specimens. |
| | | Maximum Pecent - Blue is highest, Red is middle, Yellow is lowest |

Laboratory Test #2: 0762502
Profile Study

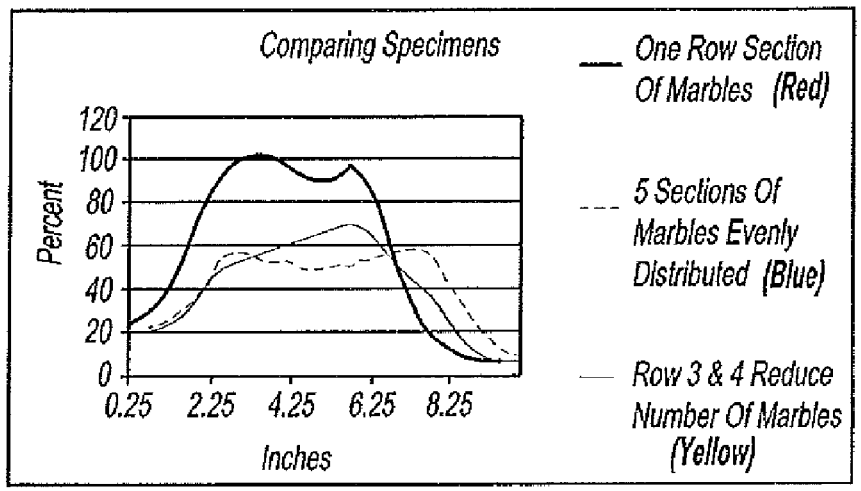

| Red profile | The red profile has five sections of equal number of marbles, two sizes. |
|---|---|
| Blue profile | The blue profile has only one section with marbles. The dip at approximately 5" is caused by this section of marbles. |
| Yellow profile | The yellow profile has two sections with reduced marble count. At 4" 15% of the marbles are removed, at 5" 25% of the marbles are removed. We see an increase in mix ratio as the tagged material replaces the reduction of marbles. At 6" the marble are returned to their original count. The profile returns to its original percentage before the the edge effect occurs. |
| Note | The design of the sensor can be adjusted to detect smaller changes. The foot print is approximately 1.5" which accounts for the reduced change in percentages. A narrow foot print will cause the dip in the black profile to fall. |
| | Maximum Pecent - Blue is highest, Yellow is middle, Red is lowest |

FIG - 26

Laboratory Test #3: 0762502
Profile Study

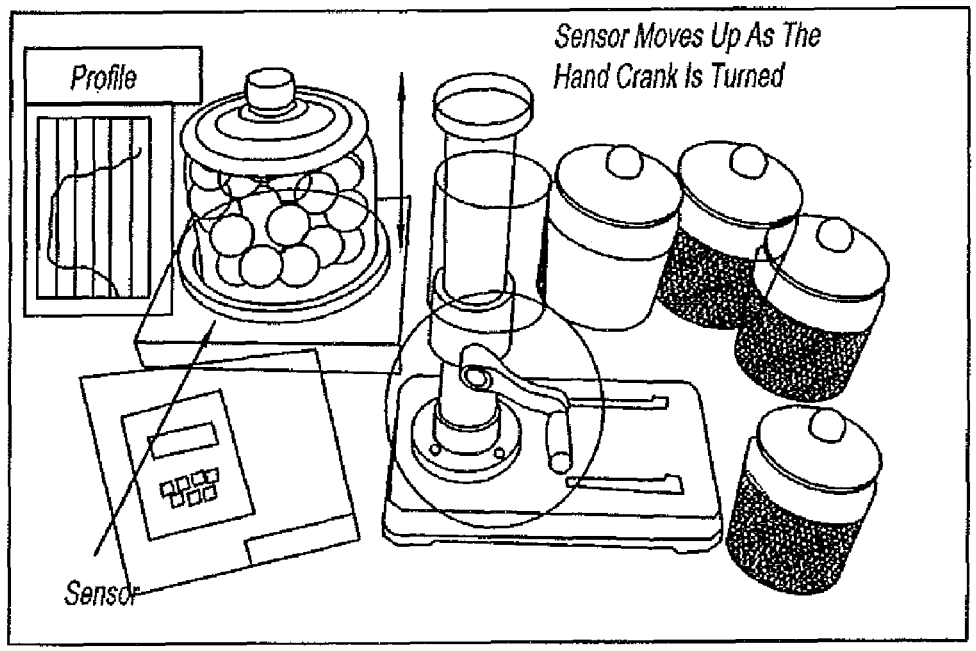
The laboratory equipment used to inspect the gelatin specimens. Each specimen is filled with a marble + gelatin + tagged material.
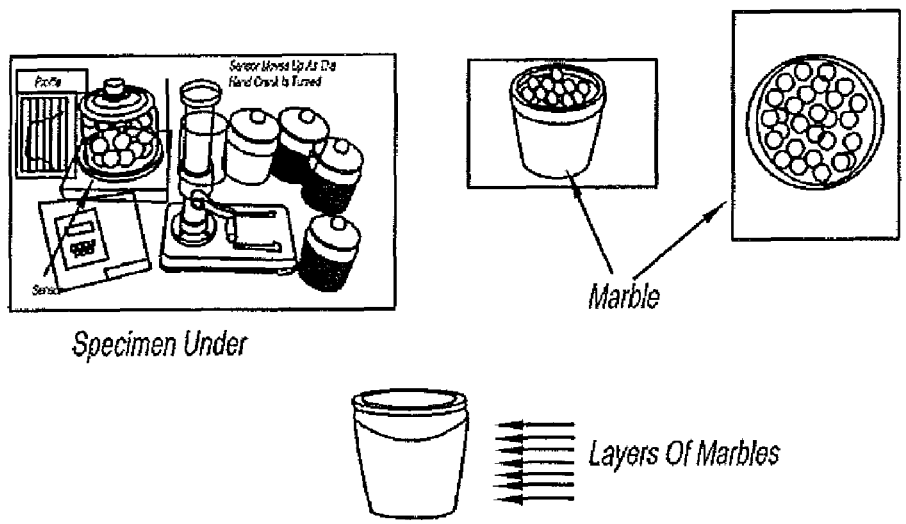
FIG - 28

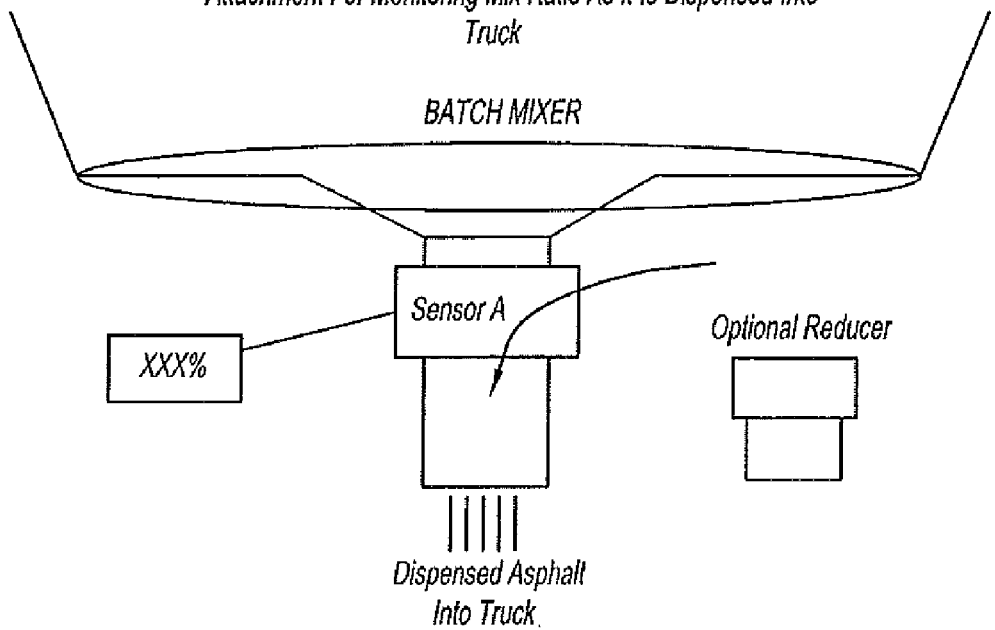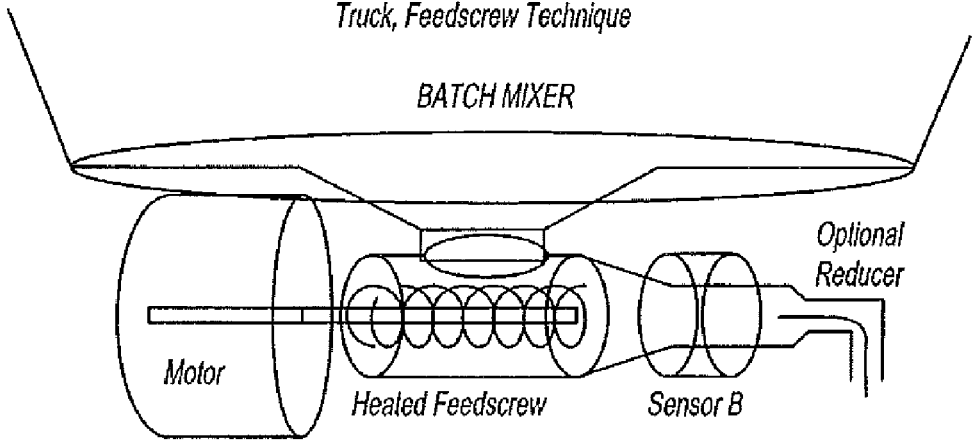
FIG-32

INSPECTION OF MIXED MATERIAL DURING INSTALLATION

CROSS-REFERENCE TO RELATED APPLICATIONS

This application is a divisional of U.S. patent application Ser. No. 11/935,605, filed on Nov. 6, 2007, now U.S. Pat. No. 7,923,992, which is a continuation-in-part of U.S. patent application Ser. No. 10/808,750, filed on Mar. 25, 2004, now U.S. Pat. No. 7,148,678, and U.S. patent application Ser. No. 11/608,979 filed on Dec. 11, 2006, now U.S. Pat. No. 7,327,136, and claims the benefit of U.S. provisional patent application Ser. Nos.: 60/864,422 filed Nov. 6, 2006; Ser. No. 60/864,479 filed Nov. 6, 2006; Ser. No. 60/870,984 filed Dec. 20, 2006; Ser. No. 60/946,447 filed Jun. 27, 2007; and Ser. No. 60/975,550 filed Sep. 27, 2007.

BACKGROUND OF THE INVENTION

The present invention relates generally to an apparatus for detecting taggants and, in particular, to a system for monitoring the ratio of mixtures formed from two or more parts.

Two-part adhesives, mixed at the time of use, are well known and are used throughout many industries to bond components together. Such adhesives exhibit a faster dry time, longer shelf life, and stronger adhesive characteristics than typical one part adhesives. One requirement of two-part adhesives is to keep the mixture of the parts at the correct ratio to obtain a reaction that will correctly form the adhesive. It often is difficult to monitor the mixing ratio in a production setting where the adhesive parts are being mixed and dispensed as needed on a manufacturing line.

A system and a method for monitoring the proportional volume of constituents provided to an adhesive mixture are shown in the U.S. Pat. No. 5,831,151. Ferromagnetic tagging material particles are suspended in one of the two constituent parts used in the mixture. A first tagging material sensor is utilized to monitor the flow of the tagged part to the mixing area and a second tagging material sensor is utilized to monitor the mixed parts as they flow to a dispenser nozzle. A monitor calculates the volumetric ratio of the two constituents based upon the concentration of the tagging material and a warning is given when the calculated ratio exceeds predetermined limits. Although the preferred embodiment of the present invention is discussed in terms of a two component mixture, this system can be used with more than two component mixtures.

SUMMARY OF THE PRESENT INVENTION

The present invention concerns a ferrous magnetic taggant system for monitoring a ratio of at least two components being combined in a mixture. The system comprises: a first sensor for generating a first sense signal representing an amount of ferrous taggant particles per unit volume of a first component flowing adjacent the first sensor; a second sensor for generating a second sense signal representing an amount of ferrous taggant particles per unit volume of a mixture of the first component and a ferrous taggant particle free second component flowing adjacent the second sensor; and a control means responsive to the first and second sense signals for calculating a ratio of the volumes of the first and second components in the mixture. The first and second sensors have a generally tubular body with a central passage through which material flows, an inner sense coil extending about a circumference of the passage, a drive coil extending about a circumference of the inner sense coil, and an outer sense coil extending about a circumference of the drive coil. The inner and outer sense coils each generate a coil signal in response to the presence of the ferrous taggant particles. The system includes an instrumentation amplifier connected to the inner and outer sense coils for generating a sense signal representing a difference between the coil signals, the sense signal being one of the first and second sense signals. The control means is connected to an information processing device and generates an output signal representing the ratio of the volumes to the information processing device.

The system includes a master for calibrating the first and second sensors, which each have a passage through which material flows. The master has a body with a smaller diameter end sized to fit into the passages and a larger diameter end sized for use as a handle. The body further having a core formed from a filler material and a predetermined percentage of the ferrous taggant particles.

The present invention also relates to a method of monitoring a volume ratio of at least two components mixed together comprising the steps of: providing a first sensor for generating a first sense signal representing an amount of ferrous taggant particles per unit volume of a first component flowing into a mixing device; providing a second sensor generating a second sense signal representing an amount of ferrous taggant particles per unit volume of a mixture of the first component and a ferrous taggant particle free second component flowing in the mixing device; and providing control means for calculating a ratio of the volumes of the first and second components in the mixture. The method further includes a step of operating the control means to compare a value of the first sense signal with a value of the second sense generated after a predetermined delay representing a time required for a portion of the first component to travel from the first sensor to the second sensor.

The apparatus and method described above can be supplemented by a third sensor where it is desirable to inspect the mixed material after the initial testing and prior to installation of the mixed material. For example, asphalt is a mixed material that may be tested at a batch mixer using the apparatus and method described above and then transported to a construction site for installation. A third sensor is provided for monitoring the taggant particles and generating a third sense signal representing an amount of the taggant particles per unit volume of the mixture flowing adjacent the third sensor, after generating the second sense signal and before completion of installation of the asphalt, to ensure a proper mixture of the first and second materials based upon the first, second and third sense signals prior to installation of the asphalt.

DESCRIPTION OF THE DRAWINGS

The above, as well as other advantages of the present invention, will become readily apparent to those skilled in the art from the following detailed description of a preferred embodiment when considered in the light of the accompanying drawings in which:

FIG. 3 is a circuit schematic for the sensor shown in FIG. 2;

FIG. 4 is a wave form diagram of the sampling of the current signal generated by the circuit shown in FIG. 3;

FIG. 8b is a perspective view of a portion of the system shown in FIG. 8a;

FIGS. 23-27 illustrate laboratory test results;

FIG. 28 illustrates an actual laboratory equipment arrangement;

FIG. 32 illustrates attachments for permanent mounting on various mixing equipment. A free flow attachment and controlled feed screw. Other constant flow devices such as piston loaded cylinders could replace the feed screw;

DESCRIPTION OF THE PREFERRED EMBODIMENT

The U.S. provisional patent application Ser. Nos. 60/864,422 filed Nov. 6, 2006;Ser. No. 60/864,479 filed Nov. 6, 2006;Ser. No. 60/870,984 filed Dec. 20, 2006; and Ser. No. 60/975,550 file Sep. 27, 2007 are hereby incorporated herein by reference.

Figure 1:
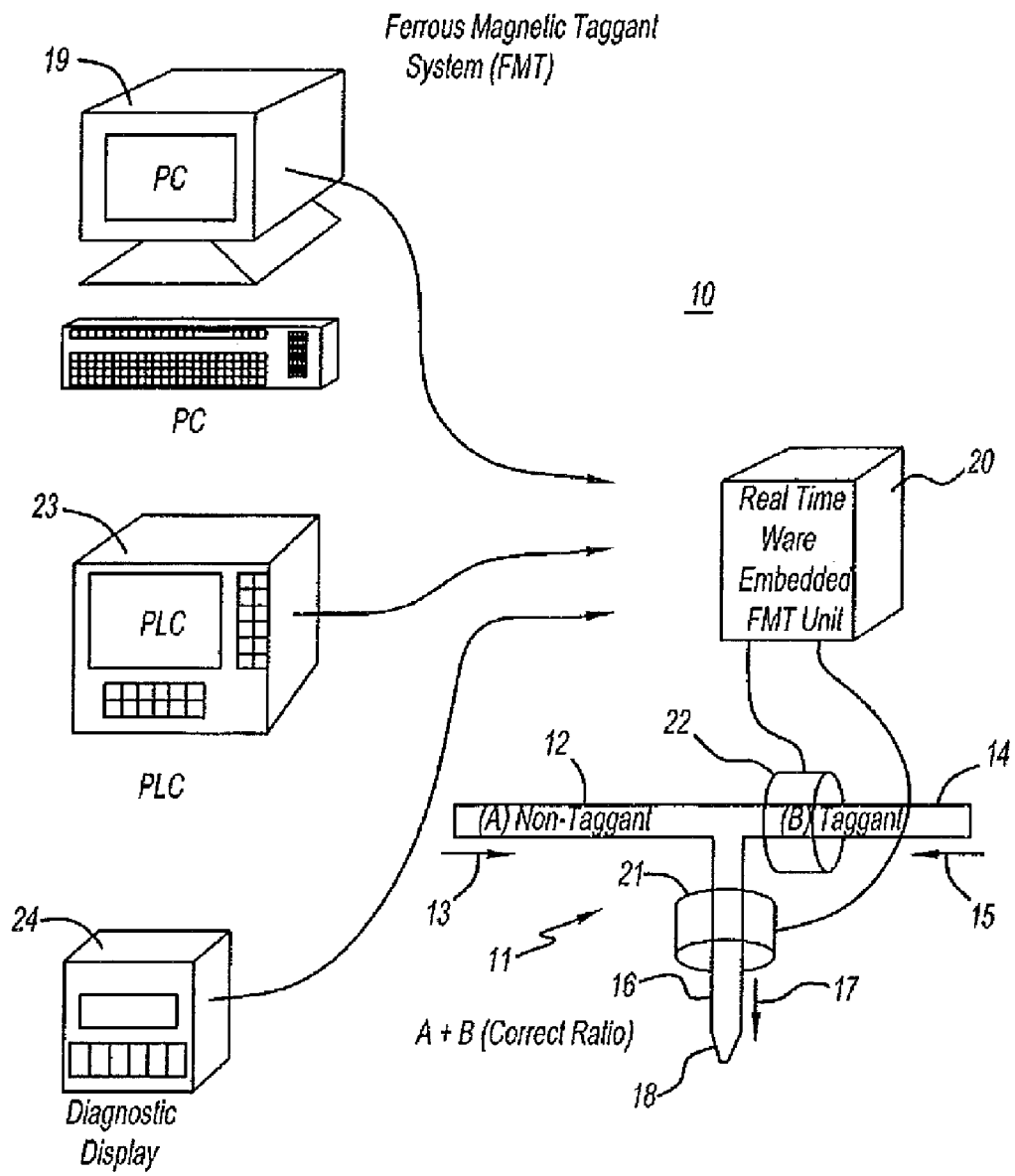
FIG. 1 is a schematic view of a magnetic taggant system in accordance with the present invention.

The present invention concerns a system for monitoring the mixing of two or more constituents to form a mixture in a desired ratio of the components. Although a two-part adhesive, a component "A" and a component "B", is used as an example in the following description of the invention, other mixtures of three or more components that either normally include or can have added thereto a metallic component that affects a magnetic field can be used with the system according to the present invention. A system 10 according to the present invention is shown in FIG. 1 as monitoring a two component mixing and dispensing apparatus 11. The apparatus 11 includes a component "A" source 12 through which flows the component "A" in the direction of an arrow 13. The apparatus 11 also includes a component "B" source 14 through which flows the component "B" in the direction of an arrow 15. The sources 12 and 14 are connected to a mixing tube 16 wherein the two components mix and through which the mixture flows in a direction of an arrow 17 to a dispensing nozzle 18. Although not shown, a conventional mixing element is positioned inside the mixing tube 16.

The system 10 includes a control means such as an electronic instrument 20 connected to two sensors referred to as sensor "A" 21 and sensor "B" 22. The sensor "B" 22 is mounted in such a manner that the component "B", carrying a constant known amount of ferrous taggant particles per unit volume, flows through the center of the sensor "B" 22. Thus, the sensor "B" 22 determines that a desired amount of taggant particles is flowing. The component "A" has no ferrous particles. When the two components are mixed in the mixing tube 16, the mixture of "A"+"B" results and flows through the center of the sensor "A" 21 to the dispenser nozzle 18. The instrument 20 can be connected to one or more information processing devices such as a personal computer PC 19, a programmable logic controller PLC 23 and a diagnostic display 24. These devices provide information as to the operation of the apparatus 11 and can use the information generated by the instrument 20 in a feedback control system to automatically adjust the flow of the "A" and "B" components from the sources 12 and 14 respectively.

The passage of the ferrous taggant particles is detected by the sensors 21 and 22 which each send a sensor signal to the electronic instrument 20. After demodulation of the sensor signal from the coil "B", a linear output signal proportional to the amount of ferrous taggant particles is generated by the electronic instrument 20. A delay representing the time required for the portion of the component "B" previously measured with the sensor "B" 22 to move within the sensor "A" 21 is required. This delay allows the taggant component "B" to mix with the non-taggant component "A" and move within the sensor "A" 21. This will assure testing of the adhesive before and after it is mixed. The change in electrical response has been determined to be linear with respect to amount of taggant. This simplifies the ratio equations. Using a deviation from a desired ratio will further eliminate errors due to different mixtures of the component "B". If for instance the mixture has been reduced by ten percent, the readings of both the sensor "A" 21 and the sensor "B" 22 will be reduced proportionally. Thus, the mixture will still have the correct ratio. The absolute reading of the sensor "B" 22 also is monitored to assure the mixture is held within a certain percent.

Equations:

EQUATION OF THE LINE: % TAGGANT=$M \times X + B$

M: slope of a line. This is adjusted with each system.

X: amplitude of the sine wave response from the A/D converter. This could also be the phase.

B: offset. This is affected by the external environment. This effect is cancelled when the coil is positioned on a production system.

$$R = \%A/\%B$$

$$\text{RATIO(DEVIATION FROM NOMINAL)} = 100 (((RAR-1)0.5)-1)$$

The constant "0.5" is dependent on the desired mix ratio. A "0.5" constant indicates two parts of the component "A" for every one part of the taggant "B". The above formula is specific to a 2:1 mixture and would be varied according to the mixture ratio be measured.

One method for making the small taggant particles is practiced by 3M, St. Paul, Minn. Small plastic balls 40 (FIG. 2) are plated with a ferrous material. This plating is noticed by an alternating magnetic field. Two effects occur: 1) the flux lines of the magnetic field are altered proportionally to the amount of the balls 40; and 2) small eddy currents are created within each ball 40 wherein these eddy currents oppose the initial magnetic field and affect the return response of the sense windings of the sensors 21, 22. Another source of taggant material is the Coat-it company.

The sensors "A" 21 and "B" 22 are made as similar as possible to cancel out variations due to the environment. By mathematically ratioing the effect to the magnetic field, the two coils cancel many common environment changes.

The present technology uses the small plated balls 40. Other taggant material may be possible. Any material affecting the magnetic field has the potential to be used.

Figure 2:
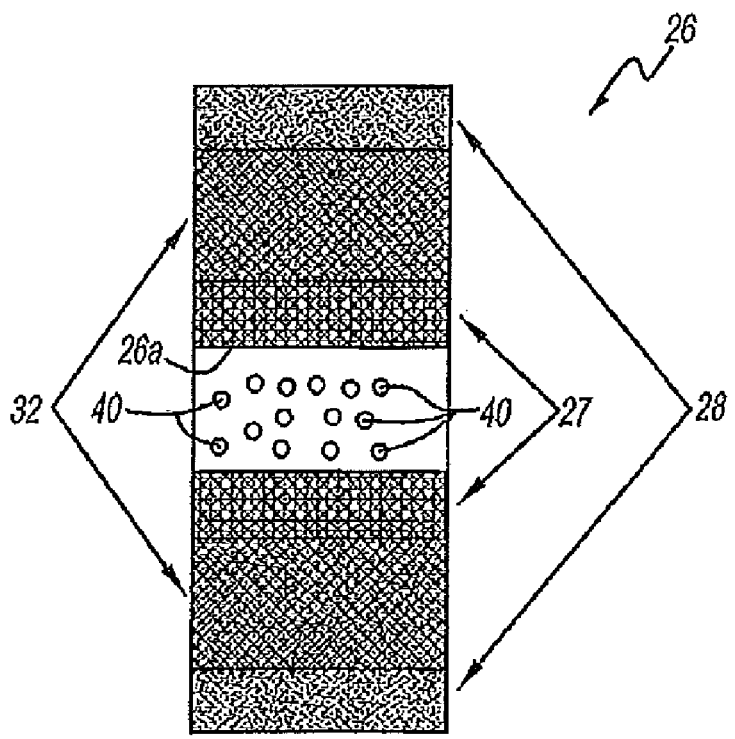
FIG. 2 is cross sectional view of a sensor used in the system shown in FIG. 1.

There is shown in FIG. 2 a sensor 26 that is suitable for use as the sensors 21 and 22. The sensor 26 is tubular in cross section with a hollow interior passage 26a through which the material carrying the balls 40 flows. Extending about a circumference of the interior passage 26a is an inner sense coil 27. Extending about a circumference of the inner sense coil 27 is a drive coil 32. Extending about a circumference of the drive coil 32 is an outer sense coil 28.

The drive coil 32 creates an AC magnetic field. The two sense windings 27 and 28 are designed so signals from the inner sense coil 27 cancel signals from the outer sense coil 28 when only air is present in the passage 26a. When material enters the passage 26a, the inner sense coil 27 receives a larger signal than the outer sense coil 28. The difference between the signals is detectable through electronics. The effect of the plated balls 40 is proportional to the amount of the balls within the sensor 26. The material used to hold the three windings 27, 28, 32 in place can be one of Delrin, ceramic, nonmagnetic stainless, and titanium. Typically, three bobbins are made, one for each coil, and tightly fit together.

As an alternative, the sensor windings 27 and 28 can be replaced by other types of sensors such as Hall Effect devices.

The electronic circuit connected to the sensor coil 26 is shown in FIG. 3. A microprocessor controlled AC sine wave oscillator 25 generates a sine wave signal to a current drive amplifier 33 connected to the drive coil 32. The microprocessor can be a separate unit (not shown) or can be a microprocessor in one of the information processing devices 19, 23, 24. The oscillator also provides synchronized square wave signals of frequencies "f" and "nf". The current drive 26 will ensure constant current on the drive side.

Changes due to the taggant 40 will occur on the sense side. The two sense windings 27 and 28 are situated in such a manner that in air there is no signal. When the metallic particles 40 are positioned inside of the coil 26, the inner sense coil 27 is more affected then the outer sense coil 28. The coils 27, 28 are connected to inputs of an instrumentation amplifier 29 that measures the difference between the two sense winding signals. A difference signal generated by the amplifier 29 is filtered by a filter 30, AC coupled and directed to an analog to digital converter 31. The signal from the oscillator 25 having the frequency "nf", typically four times a frequency of the signal "f", is applied to the converter 31.

Similar circuitry 34 is provided for a current signal from the oscillator 33. The current should be very stable. However, even small changes in the current due to power supply variation can cause variation in the return information. These effects are cancelled by normalizing the sense signal from the filter 30 with a return. The "4f" frequency signal which is synchronized at four times the sine wave frequency will provide the A/D conversion start pulses. Sampling is every 90 degrees to obtain four points for each sine wave as shown in FIG. 4 as points "p1" through "p4". Two A/D conversions, one for a current signal "Isin" and one for the sense signal "SENSE", sample at precisely the same time. The four points are used to remove any DC information and accurately calculate the amplitude and the phase of the "Isin" signal and the sense sine waves. The sense signal is divided by the current "Isin". This compensates for any deviation due to the power supply. This normalized amplitude and phase result in an electronic number proportional to the percent of taggant 40 (metallic particles) in the coil 26. It has been found that the percent of taggant 40 inside the coil 26 varies linearly. Now, the percent taggant can be calculated based on an absolute reading. The amount of taggant used and called 100% was empirically determined. This provided the starting point. To obtain a 50% mixture, 50% of the ferrous particles are mixed. Any percentage can be mixed and predicted. However, the less the taggant, the smaller the electronic signal.

Although four points per sine wave are shown in FIG. 4, the number of sampling points can be increased for additional harmonic information. Furthermore, other techniques such as quadrature demodulation could be used. Also, the phase of the signal can be used instead of the amplitude.

Extreme care is involved to keep the integrity of the sense signal. This includes the coils 27, 28 being designed differentially. They only return signals that are information. They are zeroed in air. They return signals proportional to the amount of the taggant filler 40. The two sensor coils "A" and "B" 21, 22 are designed physically the same. The two sensor coils 21, 22 are positioned as close as possible to each other so they both encounter the same changes in environment without being effected by the magnetic field of the other coil.

Two twisted pair of wires route the signal from the drive and from the difference of the two senses. Each twisted pair has its own shield. The two wires will see the same external events such as noise coupling etc. These two wires are fed into the instrument amplifier 29 subtracting the outer sense from the inner sense and eliminating any common mode noise. The electronics are mounted on a board with a printed circuit that routes the signals differentially. Special ground plane and shielding is used.

Special care is taken to remove electrical noise. Analog filters remove a considerable amount of noise. A notch filter is designed to remove the 60 Hz noise. High pass and low pass filters remove the aliasing type noises and unwanted frequency noise. Software filters further remove noise which has been picked up on the circuit board or at the last stage before the A/D conversion. These filters are optimized for a particular frequency.

A special 60 Hz filter algorithm has been developed to remove all 60 Hz noise. By selecting a frequency multiple of 60 Hz, it is possible to completely remove any 60 Hz related noise. 120 Hz noise is a common problem when considering high gain circuits. First, select a frequency at "n" times the test frequency. Example: 16×60=960. Gather four points (90 degrees apart) for 16 sine waves. Note these 16 sine waves correspond to 60 Hz since the frequency was defined as 16×60=960 Hz. Subtract the first point from the third point and the second point from the fourth for each of the sixteen 960 Hz sine waves. Now there are two points for each sine wave. This has removed all of the DC and there are sixteen pairs of points. By averaging the first of these points and then averaging the second for each of the sixteen 960 Hz sine waves, the 60 Hz noise is removed. Also improved is the variance by 1/sqrt(n) by averaging. Now the two points can be converted to the amplitude and phase of the signal.

Using the above techniques, the DC offset is removed from each sine wave. Averaging sixteen waveforms has the effect of reducing the variance due to random noise by 1/sqrt (16). Because the frequency was chosen to be a multiple of 60 Hz, also removed is the effect of both 60 Hz and 120 Hz. In Europe, a multiple of 50 Hz will be chosen.

Figure 5:
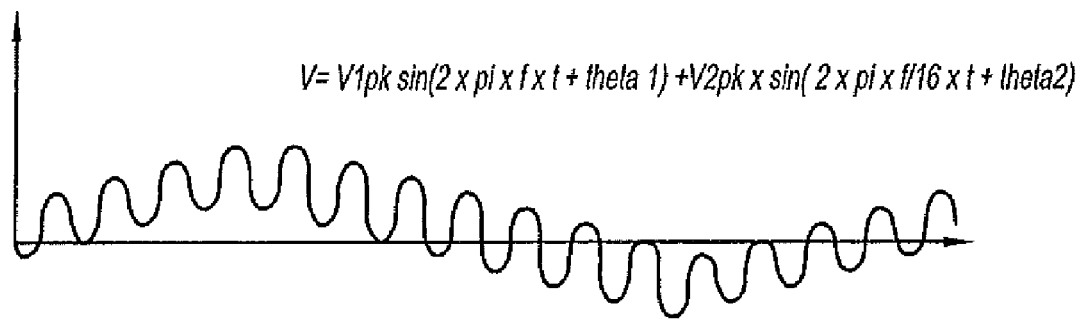
FIG. 5 is the wave form of FIG. 4 with the DC offset removed.

The waveform of sixteen sine waves shown in FIG. 5 has the DC offset removed and includes both 60 Hz and 60×16=960 Hz. As previously explained, four points are sampled for each 960 Hz waveform. Then the first, second, third and fourth points are averaged. This averaging will remove the 60 Hz, and the 120 Hz, the 240 Hz . . . until Nyquest sampling theory of less than two samples/cycle is reached. At this point other filters are removing the noise.

Automatic determination of offset: In the past the procedure would be to remove offsets caused by change in environments by manually adjusting the offset. In the system according to the present invention, the operator turns off the component "A" supply and the same material will flow through both coils 21, 22. The percent taggant should read the same for both coils. A simple calibrate offset button will remove any of the offsets. No adjustments by the operator are required.

Spacial and volumetric filter: in the past filters were all related to the frequency. The frequency has no meaning to the operator. This new algorithm will set up the filters based on the acceptable missing adhesive. For example, if one inch of missing adhesive is acceptable then a spatial filter will determine software and hardware filtering. If the operator wishes to monitor the volume flow, a volumetric filter will relate the flow rate to the frequency sampling rate etc. No knowledge of sampling theories etc. will be required.

The sampling will be related to volume flow of material or the rate of dispensing; ultimately to how much missing adhesive is allowable.

Monitoring absolute coil reading: Special algorithms will study multiple frequencies and use these frequencies to eliminate the effect of temperature. This may require fft's and regression equations to ignore temperature variation.

Figure 6:
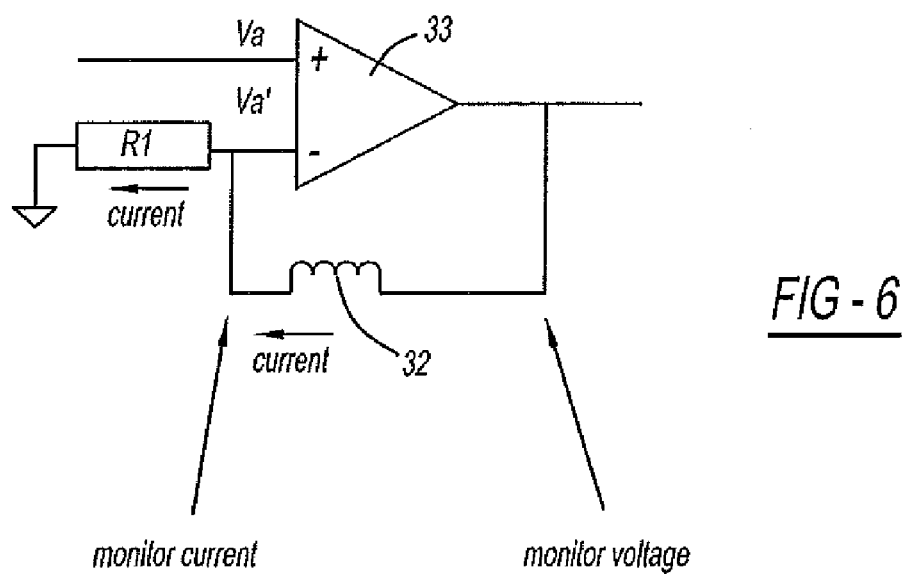
FIG. 6 is a circuit schematic of the drive amplifier shown in FIG. 3.

By monitoring the voltage on the output of the amplifier 33, see FIG. 6, it can be determined if clipping is being approached. Harmonic analysis can be used to determine if clipping is beginning. This can be used to detect changes in a malfunctioning drive.

By adding analog switches, the sense windings can be turned on and off. These switches can be added to apply voltages to the sense windings and detect changes in coil windings, broken wires and missing cables. These voltages will be used to determine if the secondary coils are correctly working.

When switching on/off the drive, extreme transients can occur resulting in wasted time before accurate data can be taken. In the past, the turn on/off circuitry was synchronized with the oscillator frequency. The actual energy causing transients occur at non-related times based on delays in circuitry, coil resistance, capacitance and inductance. A programmable delay will switch the power on or off at the minimum transient time. This will be determined by analyses of the transients (fit's, wavelets). Removing the delay optimizes the data gathering. As shown in FIG. 3, a "D" flip flop 35 is clocked by the "1" frequency signal from the oscillator 25.

Figure 7:
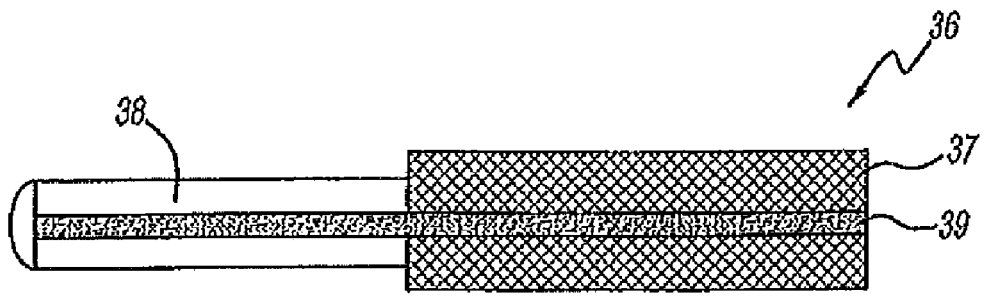
FIG. 7 is a cross sectional view of a master for the system shown in FIG. 1.

In the past, complicated masters were made using two ferrite adjustable cores. They required very stable ceramic material which was very breakable. It was sensitive with the absolute position. With the above design, the passage 26a can be filled with a master made with material similar to that used for the adhesive. In FIG. 7, there is shown a master 36 having a body with a larger diameter end 37 and a smaller diameter end 38. A core 39 extends from end to end along a longitudinal axis of the body of the master 36. The body of the master 36 can be made from a suitable material such as Delrin. The core 39 is formed of a predetermined percentage of the taggant material 40 and a filler material.

The smaller diameter portion 38 is sized to fit into the passage 26a of the sensor 26 being used as the sensor 22 for the component "B" material. The larger diameter portion 37 can be used as a handle and the smaller diameter portion 38 is inserted up to the adjacent end of the larger diameter portion 37 which functions as a stop. The larger diameter portion 37 is sized to fit into the passage 26a of the sensor 26 being used as the sensor 21 for the mixture. The smaller diameter portion 38 can be used as a handle and the larger diameter portion 37 is inserted up to the adjacent end of the smaller diameter portion 38 which functions as an indicator. Typically, the diameters of the passages 26a are sized proportionally to the percentage of the component "B" in the mixture.

Figure 8A:
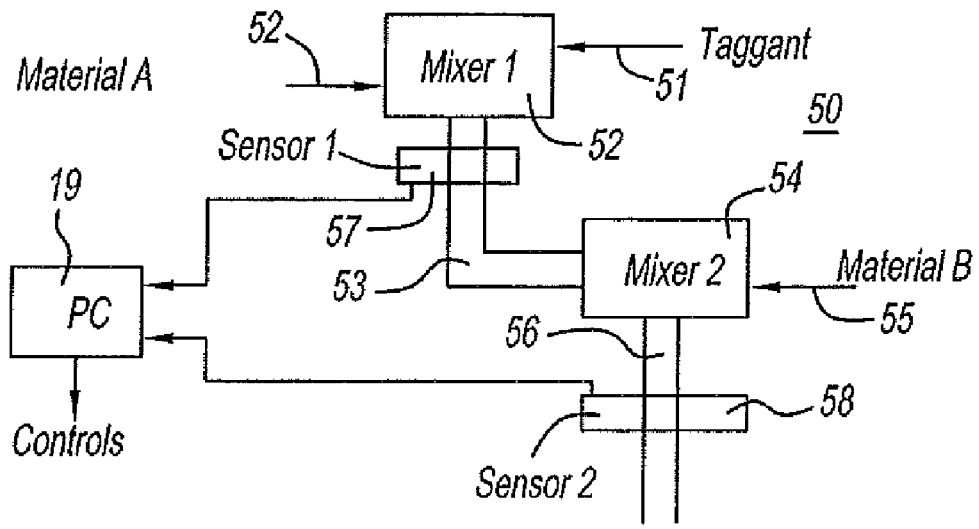
FIG. 8a is a schematic view of a magnetic taggant system according to the present invention for mixing asphalt.

The magnetic taggant system according to the present invention can be used to achieve the proper mixing of the constituents of paving and building materials such as asphalt, cement and concrete. For example, FIG. 8a is a schematic view of a magnetic taggant system 50 according to the present invention for mixing asphalt. A taggant material is supplied from a first source 51 and a material "A" is supplied from a second source 52 to a first mixer 52. The combined materials from the first mixer 52 flow through a first conduit 53 to a second mixer 54 where a material "B" is added from a third source 55. The materials are mixed to form asphalt which flows from the second mixer 54 through a second conduit 56. A first sensor 57 is provided at the first conduit 53 and a second sensor 58 is provided at the second conduit 56. The sensors 57 and 58 are operated in a manner similar to the sensors 21 and 22 of FIG. 1 to generate signals representing the mixture ratio of the materials "A" and "B". The computer system 19 can respond to the signals to generate an indication of the mixture ratio and to control the flow of the taggant material and the "A" and "B" materials.

Figure 8B:
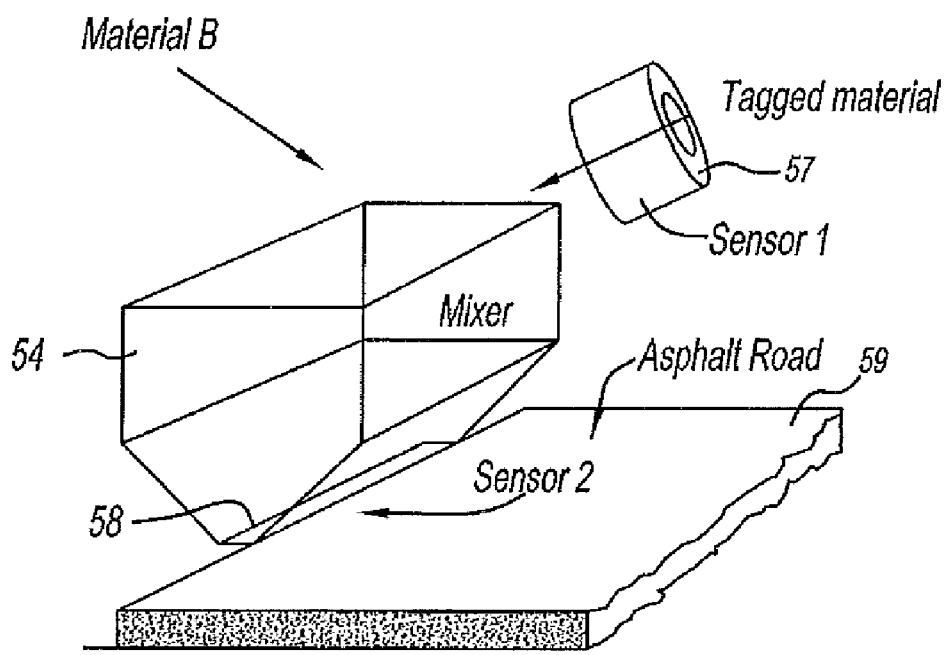

FIG. 8b is a perspective view of a portion of the system shown in FIG. 8a. The asphalt flowing from the second mixer 54 can be used to pave a road 59, for example.

Figure 9:
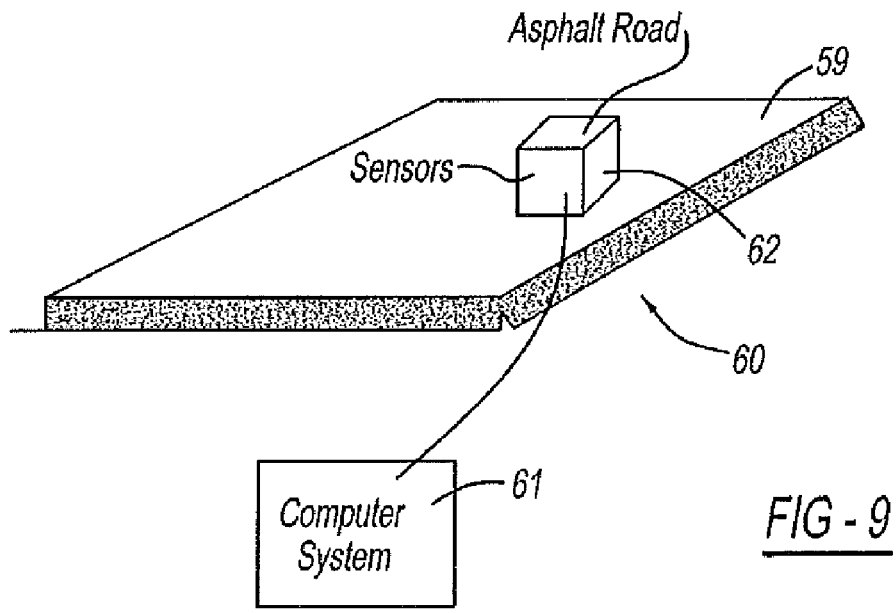
FIG. 9 is a view of a checking system according to the present invention for verifying the asphalt mixture forming the road.

FIG. 9 is a view of a checking system 60 according to the present invention for verifying the asphalt mixture forming the road 59. The system 60 includes a computer 61, typically a portable computer, connected to one or more sensors 62 that detect the taggant material. The system 60 can be used to spot check the road 59 or be mounted on a moving vehicle (not shown) to scan the road. In this manner, the asphalt mixture can be verified and the depth of the asphalt can be determined.

Figure 10:
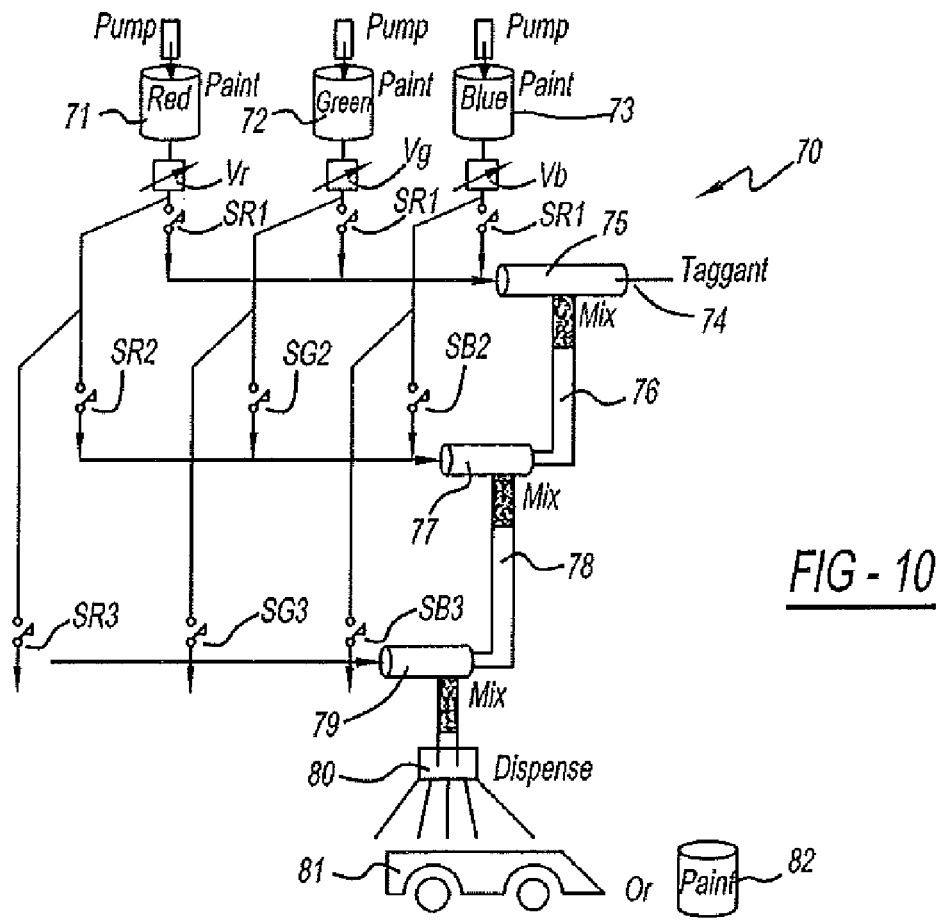
FIG. 10 is a schematic view of a paint mixing system.

The magnetic taggant system according to the present invention can be used to achieve the proper mixing of the components required to produce a desired paint color. FIG. 10 is a schematic view of a system 70 for mixing paint having, for example, three sources of paint color constituents. A red paint color source 71, a green paint color source 72 and a blue paint color source 73 have outlets connected to flow controls Vr, Vg and Vb respectively. A taggant material source 74 is connected to an inlet of a first mixer 75 having an outlet connected to a first conduit 76. The first conduit 76 is connected to an inlet of a second mixer 77 having an outlet connected to a second conduit 78. The second conduit 78 is connected to an inlet of a third mixer 79 having an outlet connected to a dispenser 80.

The paint sources 71, 72 and 73 are connected to respective inlets of the first mixer 75 by valves SR1, SG1 and SB1 respectively. The paint sources 71, 72 and 73 are connected to respective inlets of the second mixer 77 by valves SR2, SG2 and SB2 respectively. The paint sources 71, 72 and 73 are connected to respective inlets of the third mixer 79 by valves SR3, SG3 and SB3 respectively. The dispenser 80 dispenses the mixed color paint by, for example, spraying the paint on a car body 81 or filling a paint can 82.

Figure 11:
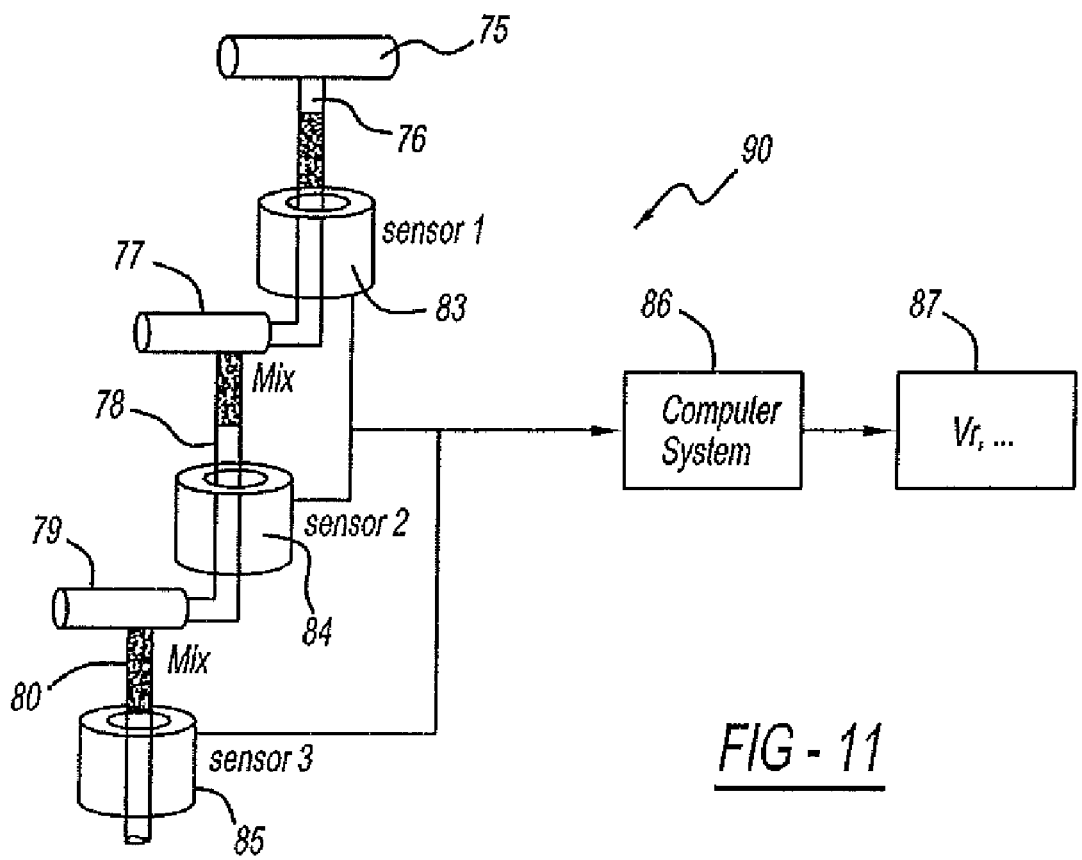
FIG. 11 is a schematic view of a magnetic taggant system for controlling the mixing of the paint in the system shown in FIG. 10.

FIG. 11 is a schematic view of a magnetic taggant system 90 for controlling the paint mixing in the system shown in FIG. 10. A first sensor 83 is provided at the first conduit 76, a second sensor 84 is provided at the second conduit 78 and a third sensor 85 is provided at the third conduit 80. The sensors 83, 84 and 85 generate signals to a computer system 86. Based upon the signals from the sensors 83, 84 and 85 and information about the desired color mix, the computer system 86 controls the operation of a plurality of devices 87 in the system 70 which includes the flow controls Vr, Vg and Vb for regulating the flow rate and the valves SR1, SG1, SB1, SR2, SG2, SB2, SR3, SG3 and SB3 for turning on and off the flow.

Additional technologies are explained below as related to Ferromagnetic Tagging (FMT). Magnetic Flux Tagging (MFT) is a more generalized description of this technology. FMT is a subset of MFT when ferrite powders are used.

I. Lab Equipment—for Measuring Mix Ratios:

1. Equipment will monitor the mixing of multiple components. A tagged material will be added to component "A". As this chemical is mixed with other materials the mix ratio will be calculated and displayed.

2. A second component "B" could also be mixed and monitored. Components "A" and "B" will have unique mix ratios. Components "A" and "B" can be mixed and its ratio can be calculated. As an example if component "A"=80% and component "B"=40% a 1:1 mixture should result in a reading of 60%.

3. Equipment will have a method to normalize any materials through mathematics. One possibility will be a linear prediction by measuring the mix ratio of two known ratios with known percentages of tagged material and then calculating a gain and offset to linear predict the mix ratio of other mixtures.

4. Equipment will have the ability to monitor a time constant of the separation of the magnetically tagged material and then predict the time constant of separation of various other materials. As an example, if the mass and specific gravity is known for the tagged material various non-metallic materials with known mass and specific gravity should have similar time constants for separation.

5. Various other laboratory aids will be included. The ability to download (or store) data at various times; for example, to monitor the separation of ferrite over time. Another possibility is to monitor a chemical; as air is removed the materials mixture will change (example—more tagged material per unit volume).

II. Monitoring of Mixing—with Chemicals which Already have a Percent of Metal Present:

Mixtures may naturally have metallic powders or metallic powders are added because they provide a desired chemical effect. This will provide the same magnetic effect as the tagged material. Additional mixing of these materials can be monitored.

III. 100% Inspection—of One Component Materials:

1. One component materials such as a one component adhesive can be 100% inspected. One component is manufactured by mixing several components. Each mixture (or critical mixtures) can be monitored. After each mixture is monitored an average value and standard deviation will describe the content of the new material shipped. The customer who dispenses this material will also monitor the dispensing to ensure the mixture has not changed.

2. The addition of thixitrope (suspension stabilizer) could also be added in a known amount to allow the tagged material to separate at a known time. This would be detected by the FMT technology notifying the dispensing equipment the shelf life has been exceeded avoiding dispensing out of spec adhesives.

IV. Phase Information:

By adding a two materials such as a ferrite and aluminum adds phase information.

This may allow unique footprint for the new mixture.

V. In Line Tagging:

Add a tagging mechanical mixer to mix the tagged powder with one of the two chemicals to be mixed. This would simplify retrofitting to existing systems and would not require the chemical manufacturer to add the tagged chemical.

VI. Portable or Light Industrial or Hobbist Equipment:

This technology can be easily adopted for portable, light industrial and hobbyist use. Low cost electronics is presently available. The design could be minimized to a cost effective way to monitor mix ratios.

VII. Add Ferrite—(or Other Magnetic Powder) to Monitor The Flow Rate of Fluids (Example, Flow Rate of Hydraulic Fluid):

1. Add hard ferrite (or any powder which can be magnetized) to monitor flow with non-contact sensor. In previous papers we discussed detection of flow rate by magnetizing a group of particles then detecting them at a known distance from the magnetization source allowing us to determine flow rate.

2. Magnetize the powder as it passes. Use a sensor placed at a known distance. Perhaps a differential coil. Record the time between magnetizing and sensor detection. If the tube is round the volume rate will be $pi \times r^2 \times distance/delta\ time$.

3. By adding two sensors it may provide a more accurate measurement. Magnetize with a slow sine wave varying frequency. Then use the sensor to measure the phase. This will be the delta time required for volume calculations.

Monitoring the mix ratio of asphalt has been problematical, resulting in major expenses when constructing roads parking lots etc. A new technology mixes tagged materials into the asphalt during the manufacturing process allowing Magnetic Flux Tagging, MFT equipment to accurately inspect the mix ratio. As the tagged material is mixed and other components are added the percent volume of tagged material is reduced. Using MFT sensors we can monitor these changes which accurately represent the mix ratio.

Various sensors have been developed which provide inspection at all stages of the asphalt manufacturing. In the laboratory we 100% inspect the batch mixing of liquid asphalt and various other components, stones, stone chips and sand as they are added. This provides us with reference information useful during the manufacturing process. Tagging allows us to 100% inspect the batch manufacturing. We can continue to examine the asphalt as it is dispensed on the roads. The finished roads can be studied for mix ratio quality with nondestructive test sensors. The same non-destructive sensors can be used on older roads to study the change of mix ratios as the concentration of stones in the asphalt began to change their position.

Presently there is no simple technology to monitor the mix ratio of asphalt. Often, weeks or months after a road is installed the road must be torn out and replaced. The present technology requires removing samples of the road as the asphalt is poured at preset distance increments. These samples are sent to the department of transportation for evaluation. The evaluation is a lengthy process further complicated by the enormous amount of construction during the busy summer months. Various test perform at the department of transportation determine whether the quality of the road is within specification. By adding the Magnetic Flux Tagging Technology all steps of the manufacturing, laboratory development, asphalt manufacturing, road construction and non-destructive testing of finished roads. The roads profile and historical data can now be accumulated for preventative maintenance and traceability.

Figure 12:
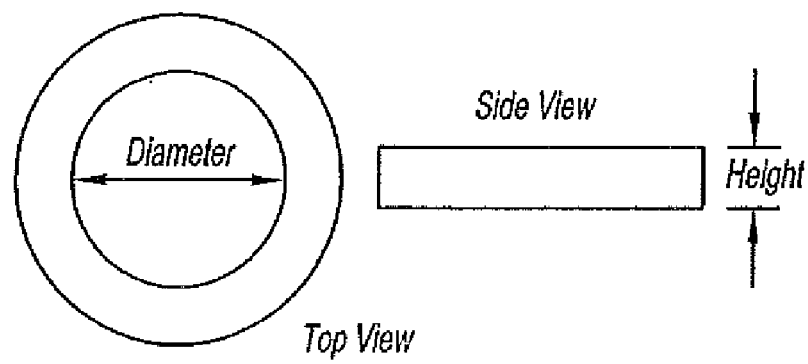
FIG. 12 is a top and side view of a temperature sensor of the present invention.

With reference to FIG. 12, the sensor of the present invention is there shown and is defined as follows.

SENSOR: A sensor is composed of a drive and sense winding. The drive winding generates an AC magnetic field. Tagged material such as ferrite powder or various metal powders are mixed with one of the components before mixing. Various sensors will be discussed. The encircling sensor has a foot print slightly larger then the volume within its cylinder. If additional material is mixed within this volume the percentage of tagged material is reduced. The reduction of material affects the mix ratio. If the sizes of particles are small then the mix ratio varies linearly with the sensors response. Large components such as stones have a similar effect by replacing tagged material with non-tagged voids. Other non-tagged voids are created when air is locked into this same volume. Other sensors will monitor the mix ratio by being placed on top of the tagged asphalt or tagged material under test. A different type sensor can be placed within the material and monitors the material around it. Alternate techniques such as using Hall Effect sensors to monitor the field are also available. By adding a temperature sensor variations in information caused by temperature variation can be compensated for.

Magnetic Flux Tagging Equipment for Mixing of Asphalt

1. Magnetic Flux Tagging laboratory equipment which provides an accurate method to ensure the mix ratio of asphalt is accurately mixed.

2. Magnetic Flux batch mixing equipment which ensures the batch mixture is correctly mixed for production. 100% inspection, control limits etc.

3. Magnetic Flux Tagging for periodic testing of batch mixture.

4. Magnetic Flux Tagging with portable equipment to periodic inspect as material is dispensed on roads etc.

5. Magnetic Flux tagging for monitoring the finished asphalt after in use with a sensor that can be positioned on top of the asphalt.

6. Magnetic Flux tagging which ensures the mixing of polymers with liquid asphalt is accurately mixed. This can also be used for subsequent mixing operations.

Figure 13:
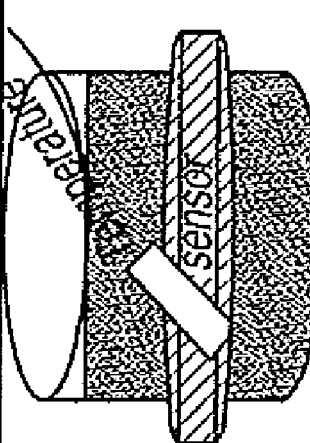
FIG. 13 illustrates different sensor types for the preferred method of the present invention.

The following description refers to FIG. 13, Sketches 1-3 and FIGS. 14-22:

1. A sensor encircles the material and determines if the material within the sensor is properly mixed. SEE SKETCH #1 of FIG. 13.

2. A sensor positioned on the material looks into the material and determines if the various components of the mixture are properly mixed. SEE SKETCH #3 of FIG. 13.

3. A sensor which can be placed inside the material to determine if the material around the sensor is properly mixed. SEE SKETCH #2 of FIG. 13.

4. A temperature sensor can be added to any of the above magnetic flux tagging sensors to provide temperature compensation information when monitoring asphalt at elevated temperature. SEE SKETCH #1, 2, 3 of FIG. 13.

5. By adding a tagged material to the liquid asphalt (binder) we can monitor each additional component as it is mixed. The sensor responds to the magnetic field proportionally to the amount of tagged material within its footprint. This varies linearly with the mix ratio when the binder+sand+tagged powder are mixed. Also changes caused by the addition of larger items such as stones, stones chips effectively replace the tagged powder with nonmetallic material which appears as void to the magnetic field and react differently the tagged material. Within the foot print less tagged material is present. This reduction in the percentage of tagged material per unit volume is detected.

6. Another method is to accurately volumetrically measure each component, add a tagged material then batch mix. The final volume will provide a percent value for the mixtures content which represents the quality of the mixture. Any deviation from this number indicates the material within the footprint is off ratio. Only the correct mixture of sand+binder±tagged material+stones+stone chips will provide a unique number.

7. Control limits can be placed on the displayed results to signal the operator the mix ratio is out of specification.

8. Distance sensor #1, #2, #3: These three sensors measure the distance above the road the Magnetic Flux Sensor is. An MFT instrument calculates the volume between the sensor and the surface. This volume is subtracted from the volume of the foot print below the MFT sensor. This sensor is optimized for looking at fields below the sensor. See FIG. 14.

Figure 14:
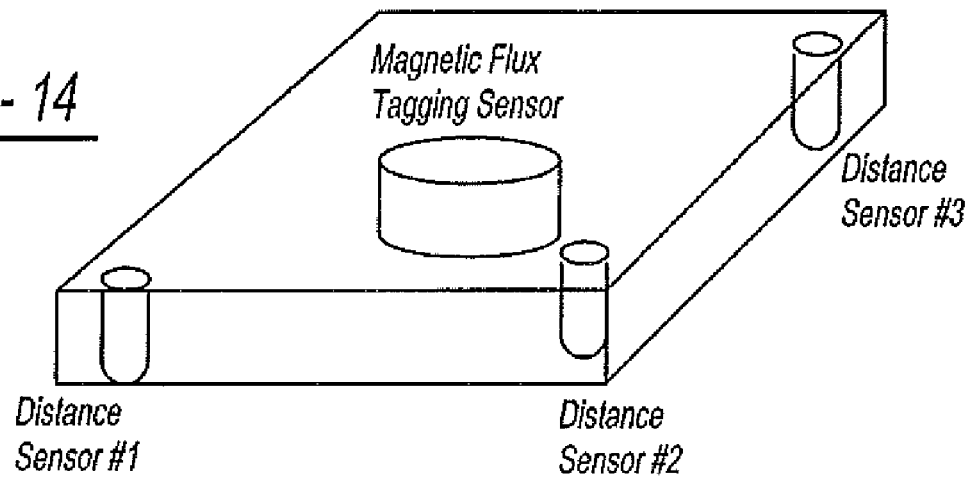
FIGS. 14-16 illustrate a magnetic flux tagging sensor used in conjunction with distance sensor.
Figure 15:
Figure 16:
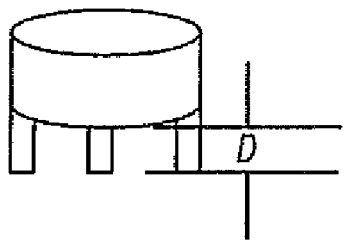
Figure 17:
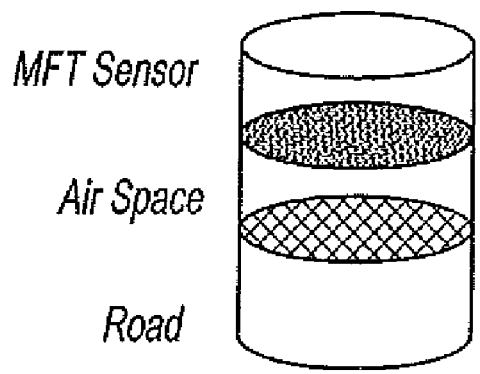
FIG. 17 illustrates an MFT sensor viewing the volume below the roads surface.

9. With reference to FIGS. 14-15, a distance sensor is positioned in center MFT sensor to calculate the distance to the road surface, volume of air, etc.

10. Spacers are positioned with the MFT sensor providing a constant distance to the road surface. The volume of air below the sensor can be calibrated out. See FIG. 16.

11. MFT sensors view the volume below the roads surface. The air space volume can be calculated and subtracted from the total volume of the MFT sensors foot print. As we analyze the road we know the mix ratio of 100% binder+sand+tagged material. The large stones and stone chips replace the tagged material with voids which are effectively spaces without tagged material. These voids reduce the mix ratio in a direct relation of the percent total volume. A stone of Ice's placed into a footprint of 10 cc's will reduce the MFT displayed value to 90%. See FIG. 17.

12. Various sensors such as ultrasonic, laser sensors can be used with moving vehicles for continuous testing of a road. Many other measuring transducers are also available.

13. The distance information can be used to adjust the drive current of the primary drive coil which creates the magnetic field we are studying. Also changing the gains of the return signal will improve the quality of the signals.

14. Wearing of road due to compacting of the materials used is also detectable through monitoring changes in the percentage of MFT per unit volume of the foot print.

Figure 18:
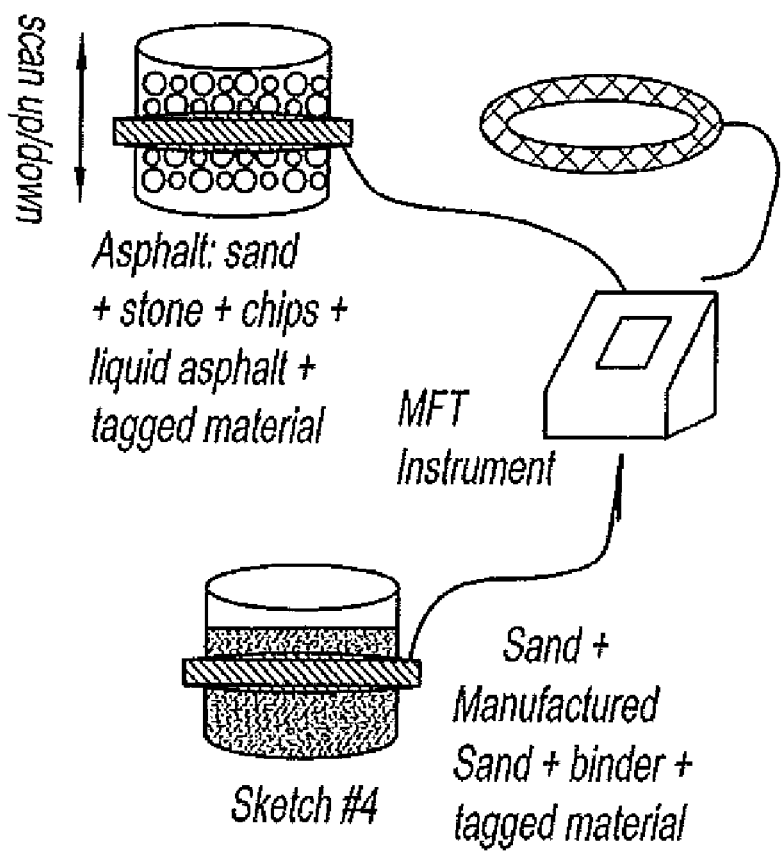
FIG. 18 illustrates a typical laboratory specimen.

15. With reference to FIG. 18, Sketch #4, LABORATORY SPECIMEN: Laboratory specimens are manufactured in laboratories by mixing liquid asphalt with stones, sand, other minerals and tagged material. They are 155 mm in diameter by 155 mm high. They are shaped as large pucks. All laboratory testing is performed through these specimens. By tagging these specimens various mix ratio information can be immediately realized. These same specimens can be further utilized to calibrate equipment used to 100% monitor the manufacturing of asphalt for final product inspection.

Figure 19:
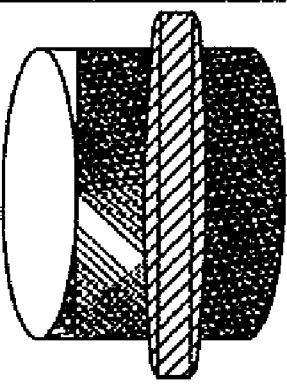
FIG. 19 illustrates a preferred embodiment of the MFT TESTING EQUIPMENT of the present invention.

With reference to FIG. 19, Sketch #5-8, a preferred embodiment of the MFT TESTING EQUIPMENT of the present invention is there shown, where:

SKETCH #5: Binder+sand+ferrite create a specimen which reads 100% with MFT.

SKETCH #6: Adding stones reduces the percentage of tagged material within the foot print.

SKETCH #7, #8: Off ratio or incorrect mixtures display off ratio values.

1. A typical asphalt mixture is a combination of sands, stones, stone chips, liquid asphalt and occasionally polymers are mixed with the liquid asphalt (binder). SEE SKETCH #6.

2. By mixing various sands and binders we can establish a reference material. By mixing a tagged material such as ferrite we can use the Magnetic Flux Tagging to monitor the mixing process. One method is to add a tagged material to one of the components and monitor how it changes after it is mixed with each additional component. Another method is to accurately calculate the volume of each component then mix with a known amount of tagged material and calculate the expected percent. For instance it is known that 2% volume of ferrite will cause the MFT system to display 100%. If we take a known volume of various materials to be mixed and add 2% of the total volume of ferrite our equipment displays 100%.

3. Two masters can be manufactured by adding 2% tagged material to master "A" (sand+binder+tagged material) the total volume and then add 1% of the total volume to second master "B". After thoroughly mixing both masters master A would read 100% while master B will read 50%. These two masters can be used to calibrate the electronics. These two masters will be used to determine the gain and offset necessary to calibrate an accurate reading in the Magnetic Flux Tagging system.

4. Once calibrated the laboratory equipment can monitor various mixtures. The variation of the display output will provide information on the volumetric mix ratio and the percent volume of the stones and stone chips has been added. When an incorrect mix ratio or volume of stone is detected the control limit will notify the operator the mixture is off ratio or the stones are not mixed. Sketch #6 is accurately mixed, Sketch #7 and #8 are inaccurately mixed.

5. A temperature sensor provides information to correct the readings at elevated temperatures. Normal batch mixing will occur at temperatures over 100 degrees C. SEE FIG. 13, SKETCH #1, #2, #3.

6. Analyzing of the material while compacting before and after provides an accurate change of concentrated material. Air voids are replaced with tagged material.

7. Height sensors can be used to calculate the total compression of a specimen when compacted. The total volume of compacted stone+tagged materials represents the total concentration of the mixture. The concentration of material within the sensors footprint monitors the mixture as it is compacted. An out of mix ratio specimen will react differently then correctly mixed asphalt.

8. MFT provides accurate concentration information by dividing the percentage mix ratio by the volume of the sensors footprint. Studying the compacting qualities of a mixture is important for road construction.

9. MFT will monitor the relation of compacting force vs. change in concentration useful in the construction of roads.

10. Measurements of the compacting force, change in overall height and change in percent mix ratio per foot prints volume are all related to the final asphalt products specification.

Figure 20:
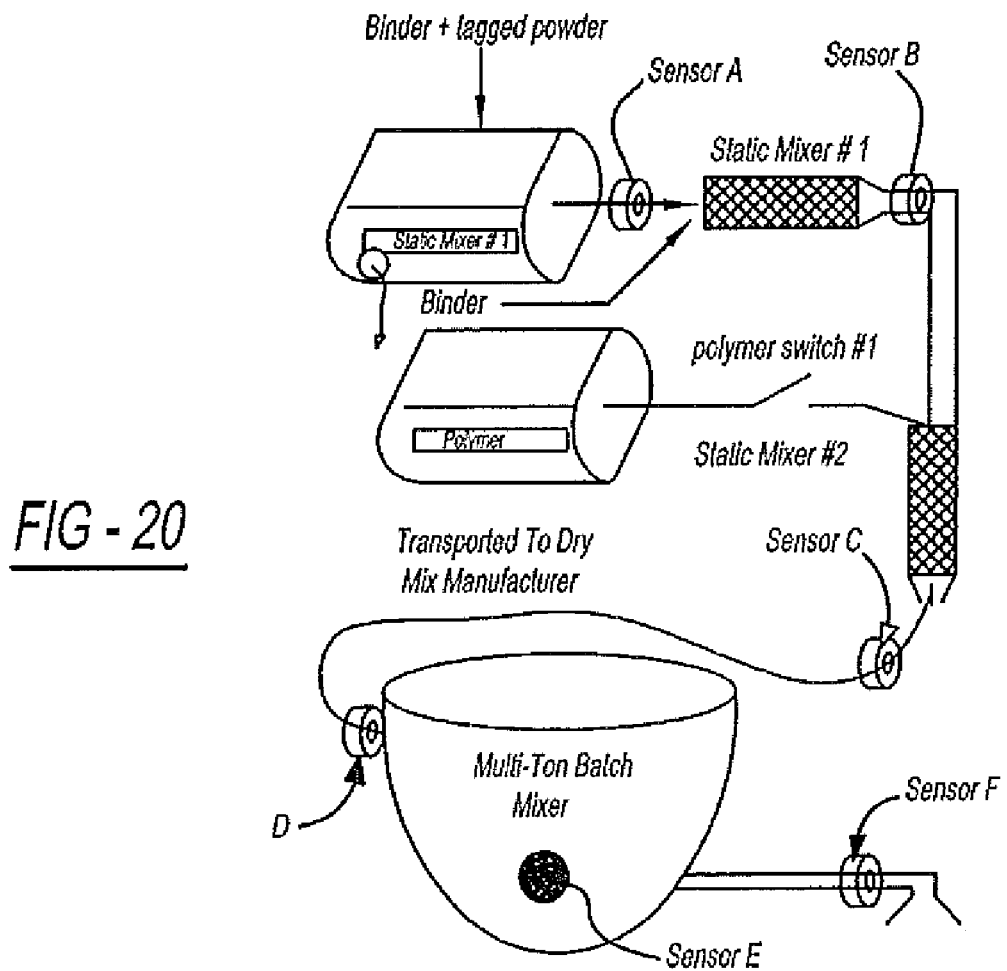
FIG. 20 illustrates a preferred method of batch testing and inspection of the present invention.

11. The non-compacted mix ratio can be used as a reference for the batch manufacturing process inspection Batch Testing Equipment, 100% Inspection and Periodic Inspection:

With reference to FIG. 20, a preferred method of batch testing and inspection of the present invention is there shown.

The binder+tagged powder are mixed. Sensor A monitors the mixing ensuring a constant mix ratio. The concentrated tagged binder will be mixed with the binder when passing through static mixer #1. The mix ratio from sensors B/A is 100% inspected. Alternately a sensor F can determine when mixer #1 is thoroughly mixed. Polymers or other additives can be mixed with static mixer #2 and monitored with sensor C. The ratio of sensor C/B is the mix ratio of polymer to binder. This is 100% inspected. The liquid asphalt or binder is typically manufactured at an oil refinery then shipped to the batch mixer where the dry mixtures are mixed with the binder. The sensor D inspects the incoming mixture for consistency' and mix ratio content. Pre-measured volumes of various mineral components such as sand, stone chips are added to the batch mixer. During mixing the sensor E help determine when the batch mixture is ready. Alternatively material can be pumped through an encircling sensor and returned to the multi ton batch mixer (not shown). When the mixing is complete the final mixture can be monitored for consistency and mix ratio by passing a continuously flowing final mixture through sensor F. The material is then transported to a construction site for instillation. Additional testing can be performed in the laboratory by utilizing MFT laboratory equipment. Another technique for periodic testing of the final batch material involves removing a sample of the final mixture and using specially designed canister with encircling coil to evaluate the sample of material. It may require pre-compacting the material to a known value to ensure the consistency is the same from periodic test to test.

POLYMER MIXING TEST EQUIPMENT: For high quality asphalt the binder is sometimes mixed with polymers. Typically a static mixer is provided at the liquid asphalt manufacturer. By tagging either the polymer or liquid asphalt the mix ratio can be 100% inspected. Ensuring the more expensive polymer mix is accurately mixed.

Polymer or other additives can accurately be added to the binder through static mixer #2.

TAGGING THE LIQUID ASPHALT: One example, liquid asphalt (binder) can be tagged by mixing the tagged material with a known amount of binder using a batch mixer. The addition of two sensors A and B will ensure the final binder is properly tagged.

TAGGING BY VOLUMETRIC CALCULATION OF BATCH MIXER: If we add tagged material as a percentage of the final mixture we can study the mixture with sensor E and then 100% inspect the material with sensors A and F as it is dispensed. The average MET value and standard deviation represent the quality of the mixture.

Figure 21:
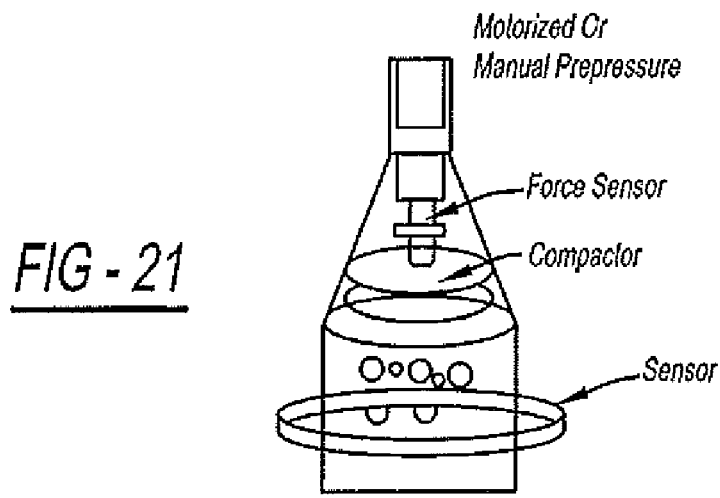
FIG. 21 illustrates placing a sample of final asphalt mixture inside of a container.

PERIODIC ROAD TEST: With reference to FIG. 21, placing a sample of final asphalt mixture inside of a container as shown and pre-compacting as determined with laboratory testing the sensor will monitor the mix ratio under a known condition. The compacting can be a manual or automatically applied.

SENSORS INSIDE THE MIXTURE: Provide mix ratio information as the material is mixed. SENSOR E.

Figure 22:
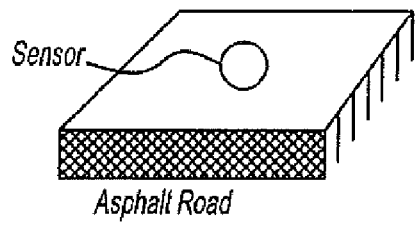
FIG. 22 illustrates Magnetic Flux tagging sensors placed on a finished surface and used to monitor the asphalt below the surface.

ABOVE SURFACE SENSORS FOR REVIEWING THE FINISHED PRODUCT: With reference to FIG. 22, Magnetic Flux tagging sensors can now be placed on a finished surface and used to monitor the asphalt below the surface. A periodic test gathers information for preventative maintenance. As the heavy loads alter the concentration of material the information will be gathered and used to prevent failures. A finished road or parking lot can be nondestructively tested by positioning a sensor on the surface and monitoring the material below the surface.

Asphalt Specimen Testing

Our laboratory testing demonstrates the value of using Magnetic Flux Tagging of the present invention for inspection of asphalt specimens. By using this technology the operator will immediately know if the specimen under test is properly mixed without destroying the specimen. A profile of the specimens mix ratio is immediately available without laboriously melting and separating the components to obtain the volumes of various components, stones, sand etc. Plastic and elastic characteristics can be viewed in real time as the specimen is compressed. The position of the off ratio can aid in understanding failures.

We have developed a method for manufacturing temporary specimens which for purpose of these laboratory experiments allows us to accurately calculate the volume and mix ratios. By using gelatin and marbles we can accurately and quickly test the various mix ratios of specimens. The use of marbles allows us to accurately measure the volume $4/3\ \pi r^3$, and use the result to determine the accuracy of the mix ratios. Various gelatin specimens will be demonstrated.

We are also interested in working with asphalt manufacturers in adapting our sensor to the actual manufacturing process. The encircling sensor we presently use can be used for 100% inspection with the final mixture as it is loaded into trucks and transported to the construction site. The addition of tagged material will also allow us to analyze below the surface of a finished road. We use an above surface sensor which monitors the tagged material below the surface monitoring any changes in the mix ratio, without destroying the road. The profile can be used to monitor changes in the road and to help in preventative maintenance.

FIGS. 22-28 illustrate a preferred method and test results for asphalt testing specifically.

Laboratory testing demonstrates the value of using Magnetic Flux Tagging of the present invention for inspection of asphalt specimens. By using this technology the operator will immediately know if the specimen under test is properly mixed without destroying the specimen. A profile of the specimens mix ratio is immediately available without laboriously melting and separating the components to obtain the volumes of various components, stones, sand etc. Plastic and elastic characteristics can be viewed in real time as the specimen is compressed. The position of the off ratio can aid in understanding failures.

In a preferred embodiment, a method for manufacturing temporary specimens has been developed for the purpose of these laboratory experiments allows us to accurately calculate the volume and mix ratios. By using gelatin and marbles we can accurately and quickly test the various mix ratios of specimens. The use of marbles allows us to accurately measure the volume $4/3\ \pi r^3$, and use the result to determine the accuracy of the mix ratios. Various gelatin specimens will be demonstrated.

The method may also be adapted for use of a sensor in the actual manufacturing process. The encircling sensor presently used can be used for 100% inspection with the final mixture as it is loaded into trucks and transported to the construction site. The addition of tagged material will also allow us to analyze below the surface of a finished road. An above surface sensor may be used to monitor the tagged material below the surface monitoring any changes in the mix ratio, without destroying the road. The profile can be used to monitor changes in the road and to help in preventative maintenance.

Figure 23:
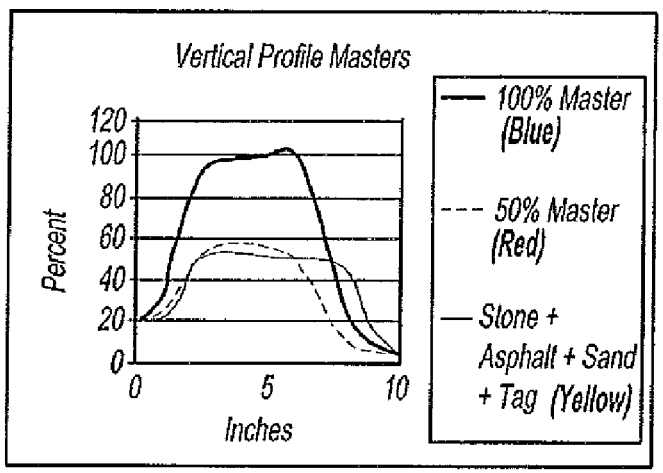

With reference specifically to FIG. 23, Laboratory Test #1 results are illustrated. The two masters are used to calibrate the sensor which varies linearly with the amount of tagged material. As stones sand etc. replaces the tagged asphalt the percentage varies linearly with the amount of asphalt replaced. The yellow profile results from filling a specimen with 1" diameter marbles and the 100% tagged asphalt. This represents the base line of the mixed marbles and asphalt.

In order to verify in our laboratory a gelatin was used in place of the liquid asphalt. This enabled the technician to quickly reproduce the specimens with various mix ratios. The same results are expected when mixed with the liquid asphalt. In this instance, marbles are used in place of stones to more easily and accurately calculate their volume, $4/3\ \pi r^3$.

Figure 24:
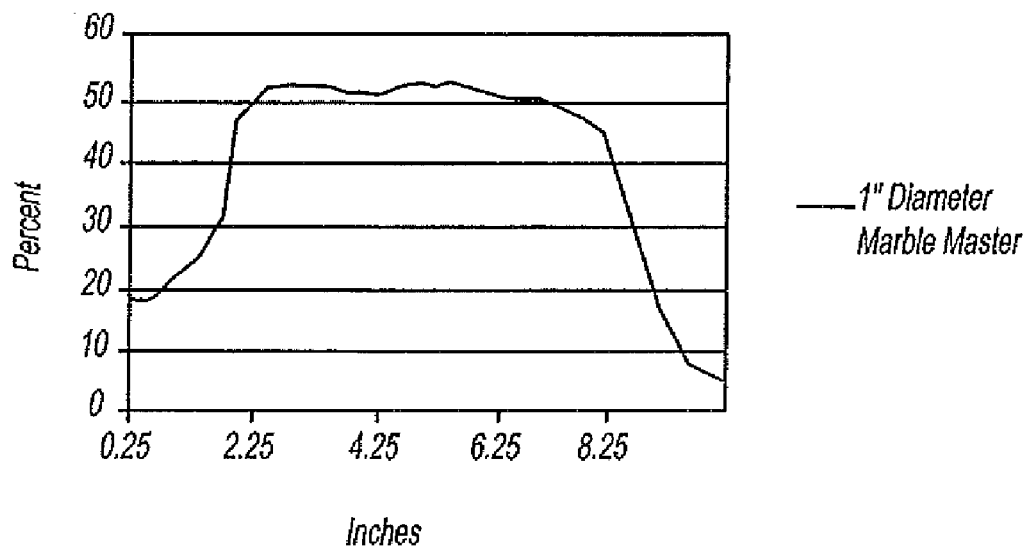

BASELINE: FIG. 24 illustrates the master filled with 1" marbles will be used as for comparing the various specimens.

Figure 25:
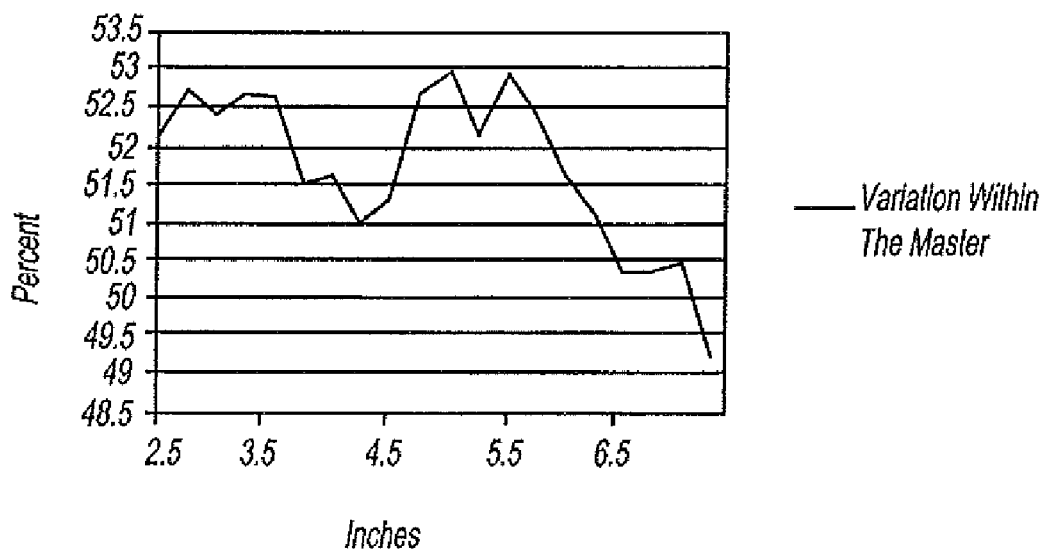

With reference to FIG. 25, the actual variation within the 1" marble master specimen can be amplified to further study how the mix ratio varies within the specimen. Note: This is an amplified profile; the full scale covers about 4% total variation of the mix ratio.

With reference to FIG. 26, three specimens have been manufactured by adding different percentages of stone. The specimens are made of five sections. The red profile has five sections of equal number of marbles, two sizes. The slight dip can be accounted for by the spacing between the marbles which are separated with 100% tagged material. The blue profile has only one section with marbles. The dip at approximately 5" is caused by this section of marbles. The yellow profile has two sections with reduced marble count. At 4" 15% of the marbles are removed, at 5" 25% of the marbles are removed. Again we see an increase in mix ratio as the tagged material replaces the marbles. At 6" the marbles are returned to their original count. The profile returns to its original percentage before the edge affect occurs.

Figure 27:
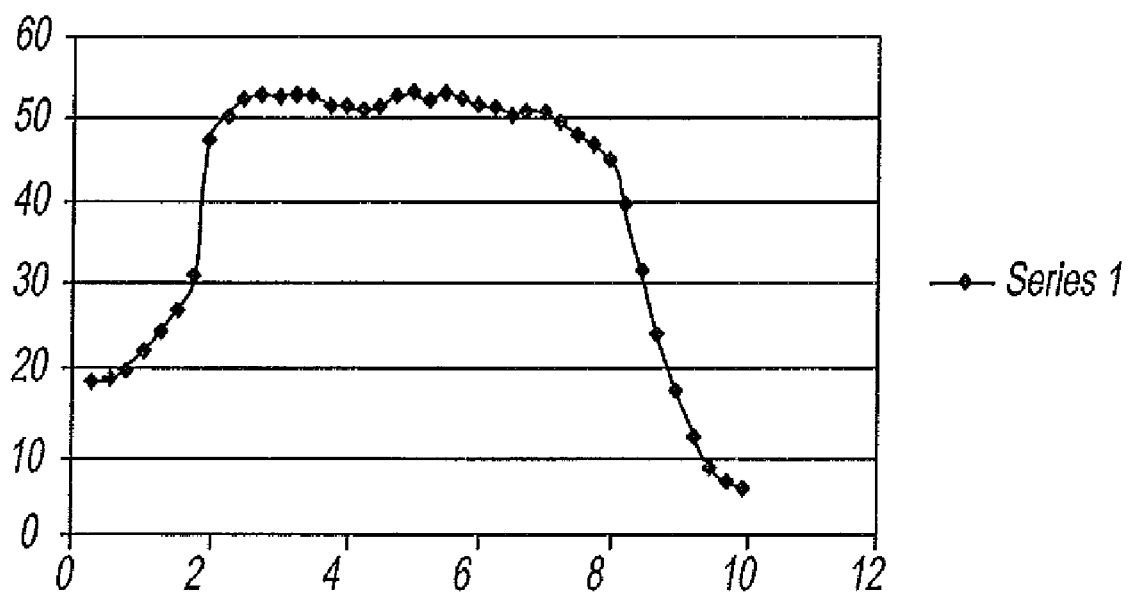
Figure 29:
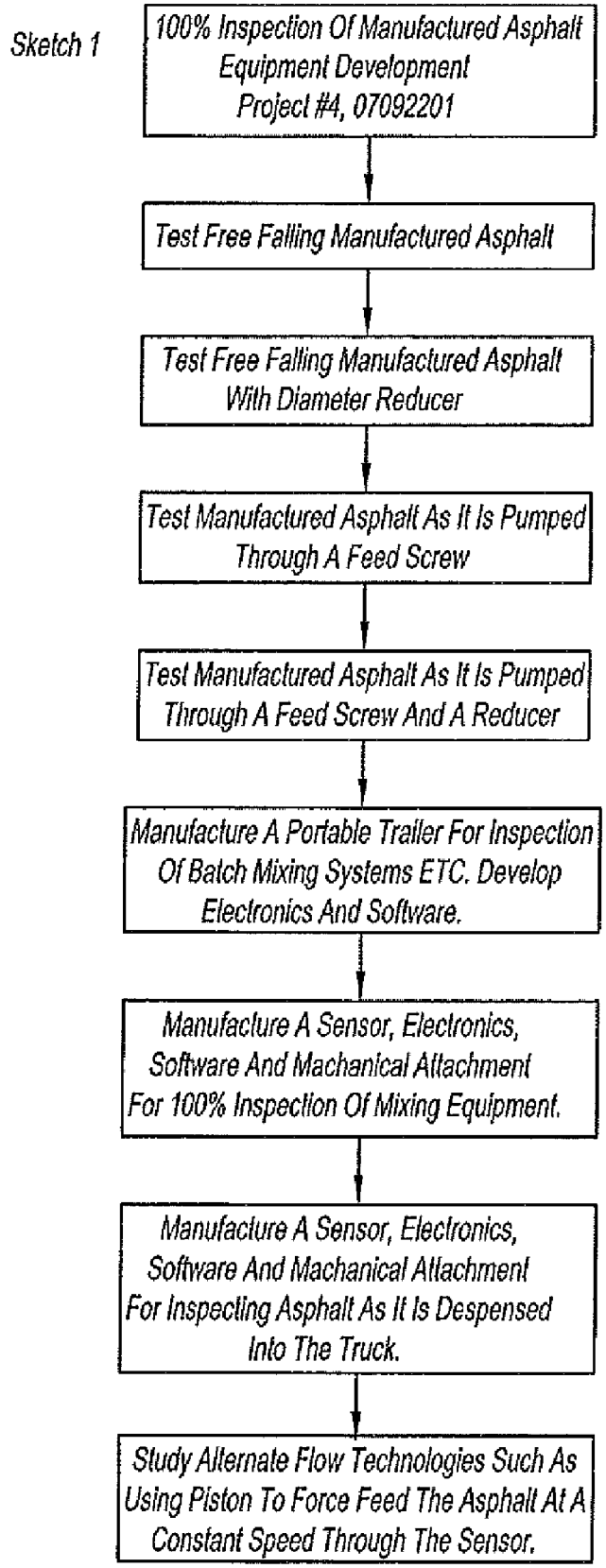
FIG. 29 illustrates a flow chart providing a description of testing.

With reference to FIG. 27, the specimen was filled with marbles of equal size then filled with 100% tagged liquid asphalt. The slight ripple at the top indicates slight variations in the mixture at these positions.

FIG. 28 illustrates an actual laboratory equipment arrangement. In this example, the jar is filled with 1" diameter marbles, each marbles volume is $4/3\ \pi r^3 = 0.52$ cubic inches each marble will require 1 cubic inch of space, 0.48 cubic inches of empty space will be filled with 100% tagged material. The ratio of tagged material is $0.48/1.00 = 48\%$. The actual displayed values varied from 49% to 52%.

We have accurately demonstrated the use of magnetic Flux Tagging when manufacturing specimens in the laboratory. We can adopt this technology to 100% inspect the manufacturing of asphalt by using a similar sensors to monitor the finished asphalt as it is dispensed into the trucks for shipment to a construction site. We have additional sensors which can be used above the roads surface to obtain the horizontal profile of the finished road mix ratio. The use of marbles and gelatin have aided in the laboratory experiment. Repeating this test with stones, aggregate liquid asphalt will substantiate these results. Magnetic Flux Tagging of the present invention monitors the mixing of liquid asphalt with polymers then monitors the amount of liquid asphalt replaced by stone+sand+aggregate mixtures. The profile of laboratory test specimens, manufactured asphalt and finished roads will all benefit with 100% inspection using Magnetic Flux Tagging as described above.

With reference to FIGS. 29-38, a preferred embodiment of the present invention is there shown and illustrates a method and apparatus for the inspection of asphalt during the manufacturing process. This describes the particular requirements of asphalt manufacturing but can be extended to various other manufacturing processes such as cement, concrete and other similar manufacturing processes of mixtures.

Occasionally liquid asphalt is mixed with polymer. If liquid asphalt is by itself or mixed with polymer it is referred to as the binder. Asphalt is the combination of binder+stones+sand+aggregate+etc.

1. Sensors developed for monitoring the mix ratio of asphalt. Made up of a sinusoidal driven magnetic field. A detection sensor which monitors changes in flux as the flux changes in proportion to the percent tagged material. The tagged material which varies in proportion to the volumetric percentage of the mixtures that is tagged. Sensors can be encircling, above surface or submergible. Temperature compensation will allow the operation of the sensor above 200 degrees Centigrade, typical temperatures of asphalt manufacturing.

Figure 30:
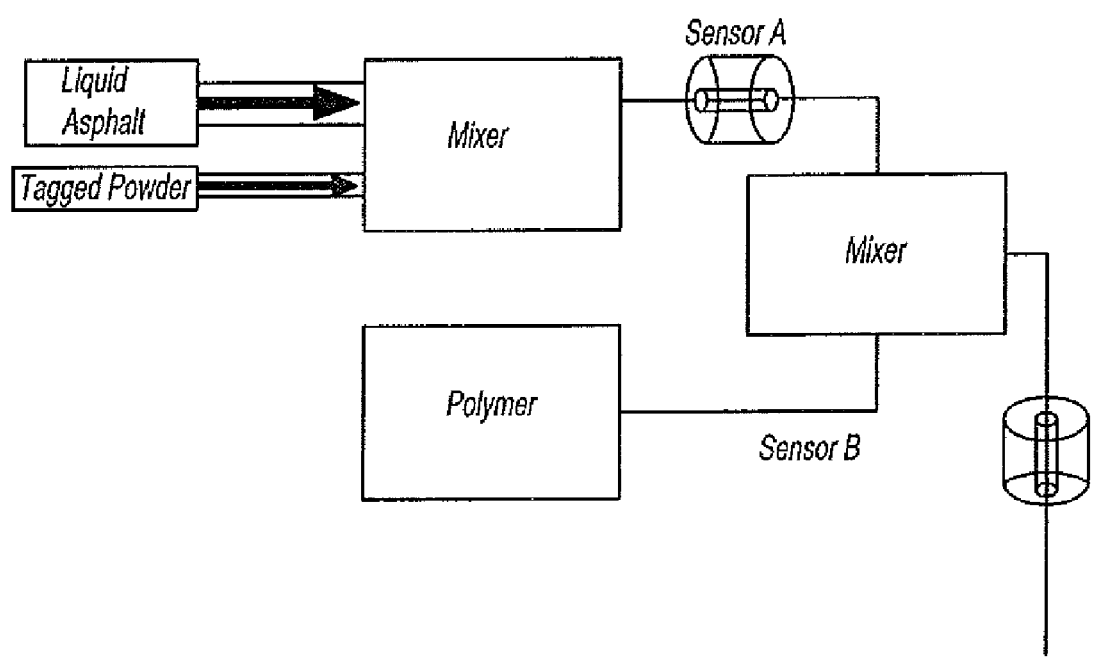
FIG. 30 illustrates a Sensor configuration at the liquid asphalt manufacturing plant.

2. FIG. 30: Sensors specifically designed to monitor the mixing of liquid asphalt with polymer, and for verification of the amount of tagged material.

3. FIG. 30: Sensors and process used at the liquid asphalt manufacturing plant to mix liquid asphalt and polymer and to ensure the proper amounts of polymer and tagged material is added and properly mixed.

Figure 36:
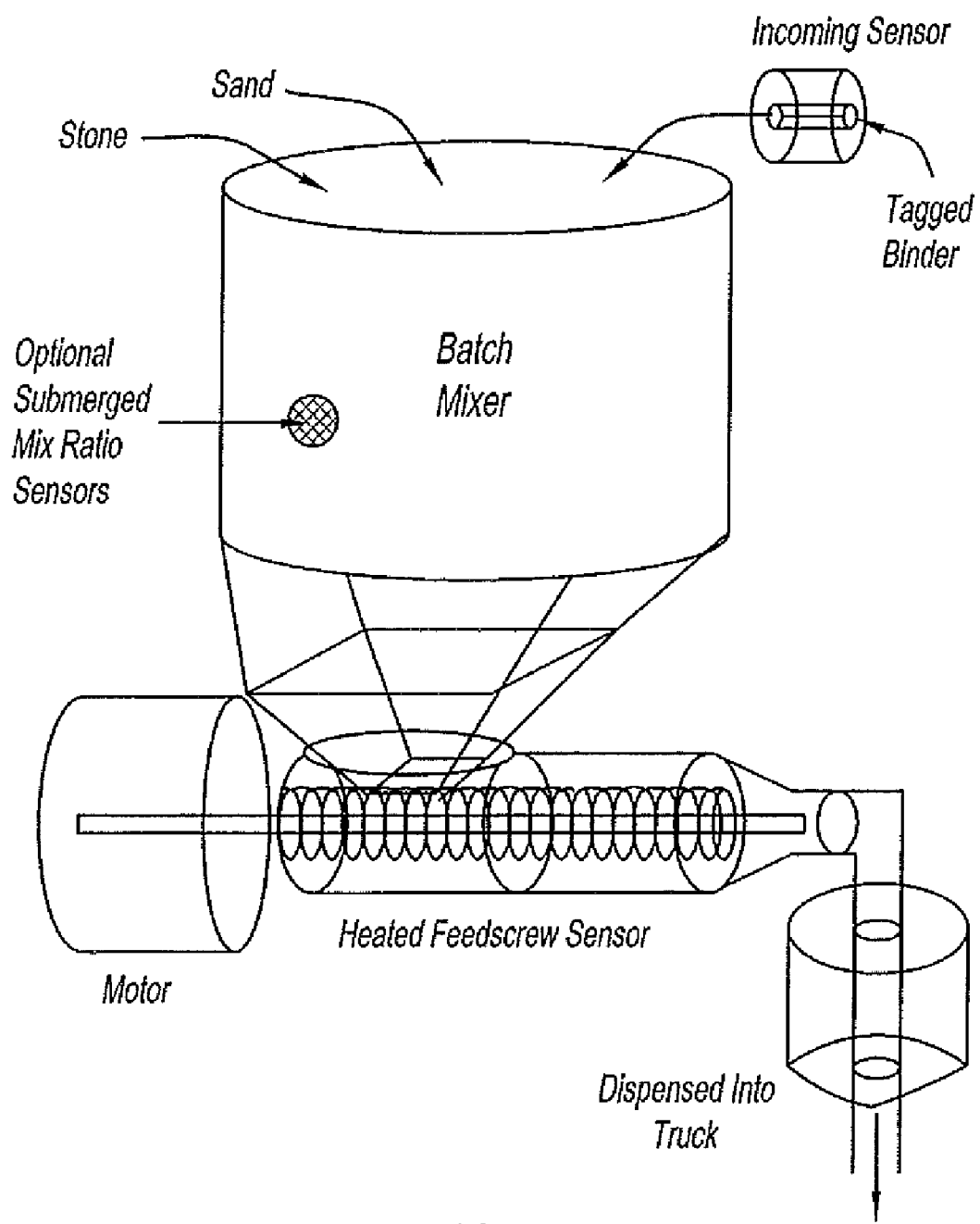
FIG. 36 illustrates a batch mixer and sensor.
Figure 37:
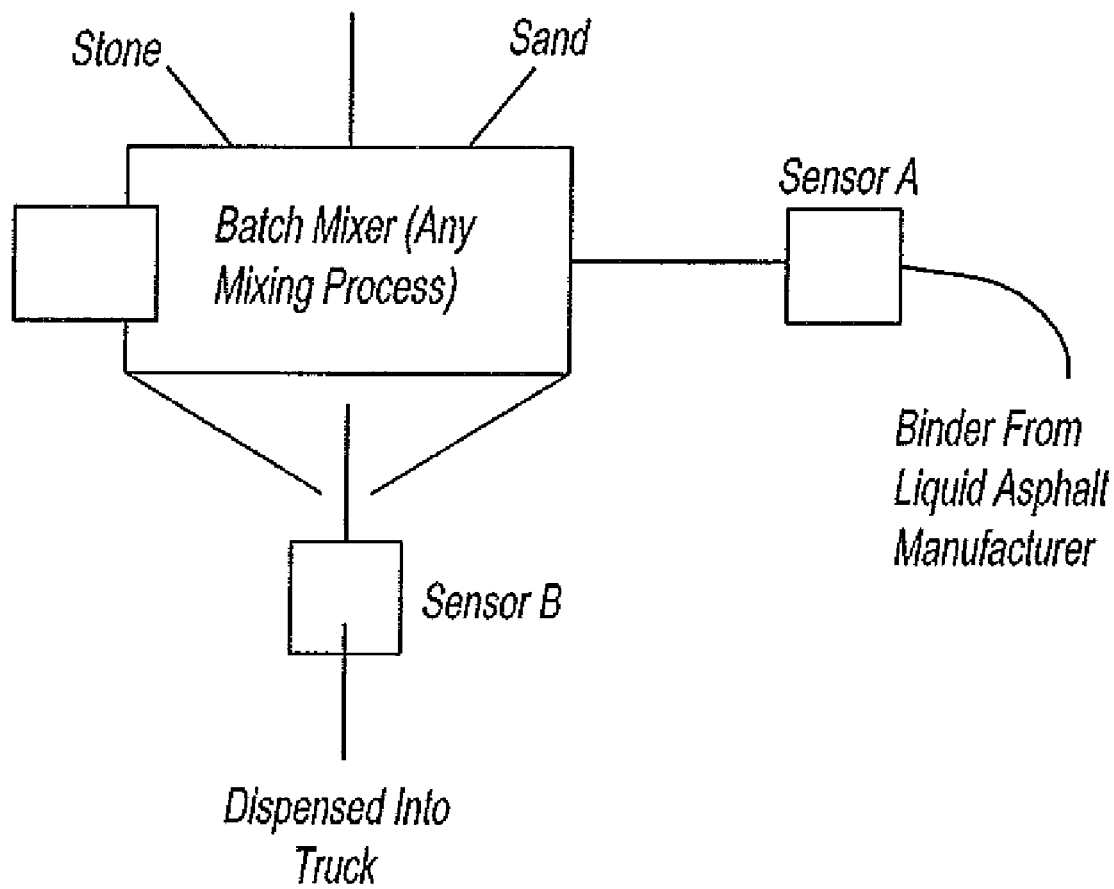
FIG. 37 illustrates a manufactured asphalt flow diagram.

4, FIGS. 36 and 37: An incoming sensor located at the asphalt manufacturing plant to ensure the correct binder mixture is received.

5. FIG. 32: Sensor and mounting hardware which 100% inspects the manufactured asphalt as it leaves the mixer.

Figure 31:
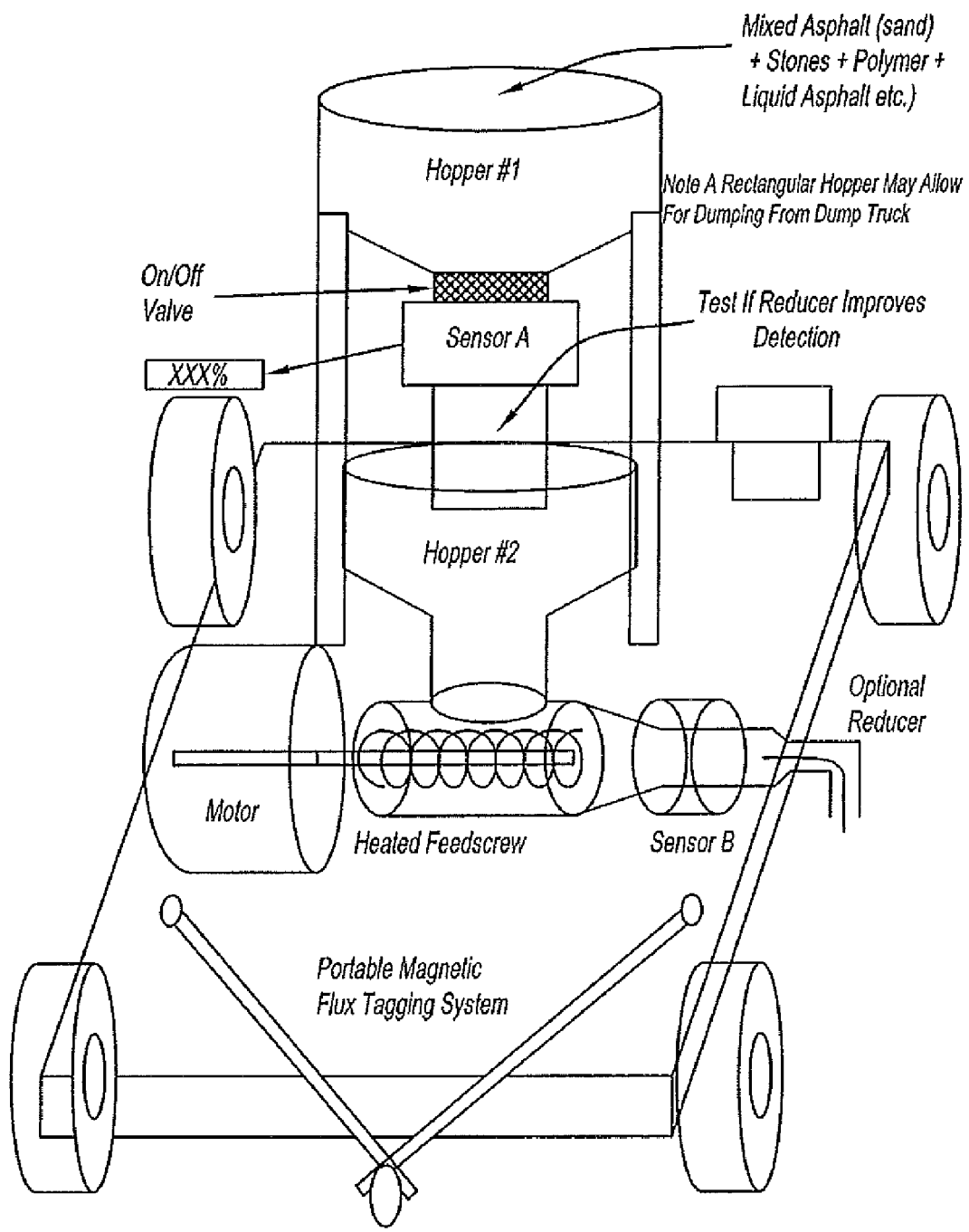
FIG. 31 illustrates a two tier hopper with optional reducers for thorough test of flowing material and with heated feed screw and reducer for more controlled flow of asphalt.
Figure 33:
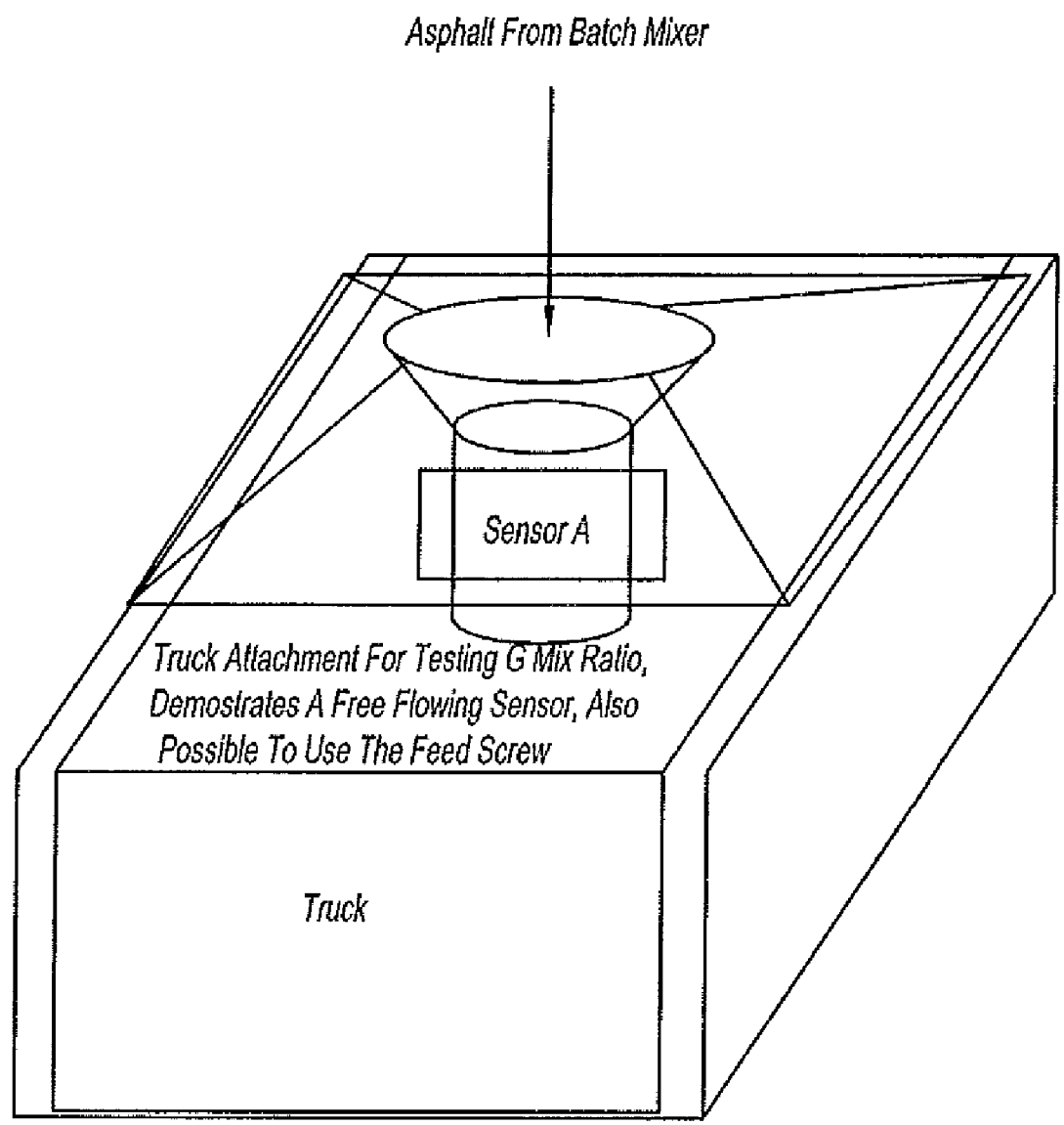
FIG. 33 illustrates attachment for truck which could incorporate any of the sensors previously described.
Figure 34:
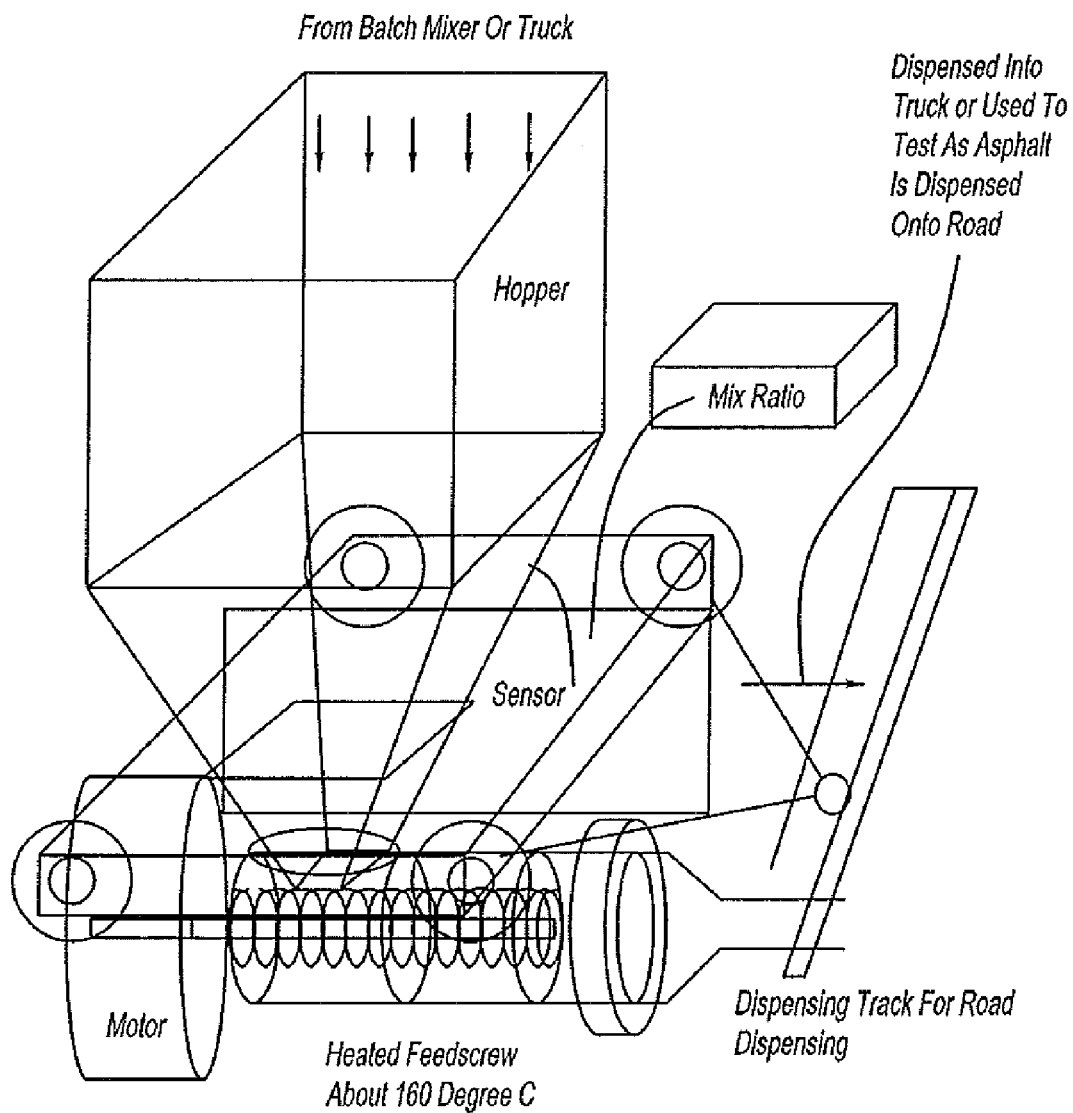
FIG. 34 illustrates a square hopper for easy dumping at a construction site. Portable mix ratio tester.

6. FIGS. 31 and 34: A portable test system which monitors the quality of the mix ratio a batch mixer or asphalt manufacturer is making. FIG. 34—A portable feedscrew is illustrated for testing quality of a batch mixer. Tagged particles are either previously mixed with the liquid asphalt or added separately directly in the mixer with sand, binder, stones, etc. The heated feedscrew provides a constant flow of hot asphalt mixtures of stone+sand+etc. The sensor monitors the mix ratio of the batch material. This will test the quality of the mixture. Various other methods of feeding a constant flow of asphalt through the sensor are possible. The feed screw assembly can be directly attached to the output spout of the giant batch mixer. Potentially, this method may be used to test asphalt as it is dispensed on the road with the addition of a gas or electric generator and an added dispensing track. Truck fill the hopper at the construction site. The material is 100% inspected as it is transferred to the road dispensing hopper. FHWA could test batch mixers by adding 0.2% by total volume and monitor how accurately is mixed—perhaps before accepting a delivery. The addition of a generator enables portable usage.

7. FIGS. 30 and 37: A process of 100% inspection by the addition of tagged material binder. Tagged material can be added at the onset to the manufactured liquid asphalt (the binder) and be evaluated at every step in the manufacturing process of asphalt. FIG. 31—Any mixing process which occurs after the tagged material is added can be 100% inspected. At the liquid asphalt plant Sensor "A" will 100% inspect the liquid asphalt after it is mixed with tagged material ensuring it is properly mixed and record the actual percentage. Sensor "B" 100% inspects the final mixture of polymer and liquid asphalt. If polymer is not added sensor "B"=sensor "A" The ratio of A/B is the manufacturing plant. The absolute value of "B" will be recorded and sent to the asphalt manufacturer. The standard deviations of the sensor "A" and sensor "B" must be within specification for accurately mixed asphalt. FIG. 37—The batch mixer is filled with stones, sand, aggregate, etc. (the components of asphalt). Sensor "A" monitors the incoming binder and verifies it matches the mixture shipped form the liquid asphalt (binder) manufacturer. Sensor "C" notifies the operator the asphalt is mixed with a submerged sensor or by pumping the asphalt through an encircling coil. Sensor "B" 100% monitors the finished asphalt mixture as ti is dispensed into a truck for delivery to the construction site. The standard deviation of sensor "C" determines if the mixture is accurately mixed. The average value is the actual mixture. By dividing C/A the actual mix ratio is calculated. This ratio can be mathematically determined by knowing the volume of materials.

8. A process of adding the tagged material directly to the mixer. It can also be added to a sub mixture for example testing the mixing of sand and manufactured sand before it is mixed with the stone aggregate. Any mixing process which occurs after the tagged material is added can be 100% inspected.

9. Sensors mounted within a hopper or inside a transporting truck for monitoring segregation. The occurrence of segregation will be detected, notifying the operator of the out of specification material before it is dispensed on the road.

10. FIGS. 31 and 34: Portable mix ratio equipment to 100% inspect or partially inspect by sampling the delivered asphalt to a construction site as it is dumped into a road compacting hopper.

11. FIGS. 31 and 34: Portable mix ratio equipment mounted on a truck or trailer which can load asphalt directly from the mixer. Move the asphalt out of the loading dock. Then perform mix ratio testing.

Figure 38:
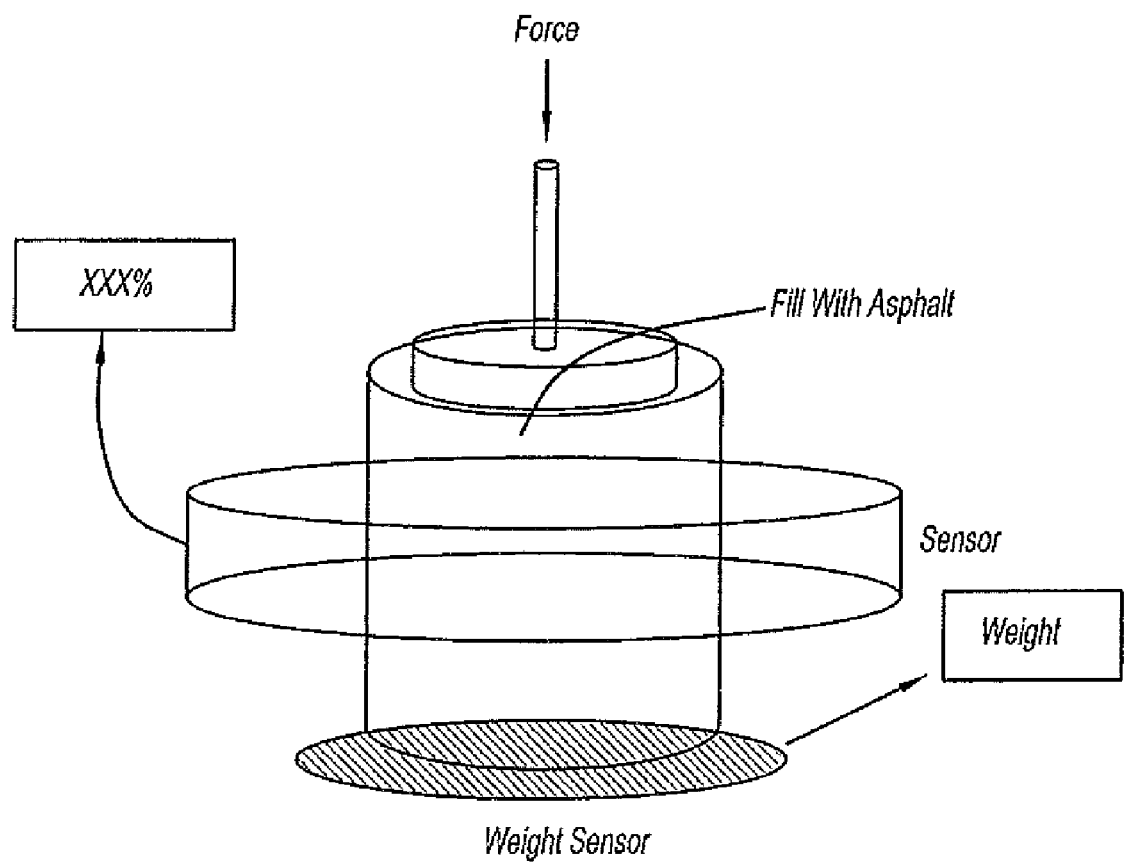
FIG. 38 illustrates a portable compactor for testing small samples.

12. FIG. 38: Various other known test can also be performed at this time for example compacting could also be tested by removing a sample, compacting to a known force and comparing to a known compacted mix ratio. In this illustration, a portable asphalt specimen is monitored. Asphalt is loaded into the mold until the desired weight is reached. After loading, a Force is applied to the asphalt through the piston type compactor. The material will be compacted to a known force and compared to a similar test performed in the laboratory. The force is applied through a lever arm or other motorized mechanism. It is a comparative test to quickly determine if the sample is within specification.

13. FIG. 32: Sensor and mechanical assembly, attached to the mixer testing the free falling asphalt as it exits the mixer.

14. FIG. 32: Sensor and mechanical assembly, attached to the mixer testing the free falling asphalt as it exits the mixer and uses a reducer to provide an evenly flowing dispensed material.

15. FIG. 32: Mechanical assembly, attached to the mixer. A feed screw or various techniques to provide a constant flow of material through the sensor for accurate mix ratio monitoring.

16. FIG. 30: Mechanical assembly performing the same test as 13 . . . 15. Designed to attach on top of a truck or various other asphalt transporting vehicles.

17. FIGS. 31 and 34: The portable equipment as described above for testing the quality of the mixture manufactured. The portable tester can be used to verify proper mixture before it is loaded onto the transporting truck. The portable tester verifies mixing equipment is correctly mixing. The same equipment can be used by organizations such as the Federal Highway Association to inspect the mixing equipment.

18. FIG. 37: Submerged sensors located inside of the mixer for monitoring the mixture as it is mixed. Other option is to pump a small sample of asphalt through an encircling sensor that will feed back into the mixer. This will detect when the mixing is completed. It can be used to notify the operator mixing is complete.

19. FIGS. 31 and 34: The test equipment will be built on a trailer allowing us to quickly download a sample of the asphalt from the giant batch mixers. After the asphalt is loaded the vehicle can be transferred outside of the loading dock where analyses of the mix ratio can be performed. This will avoid interfering with normal function of the asphalt facility. Asphalt will be dumped into the portable hopper. We will first study the affect of free falling asphalt through a sensor. A second hopper is positioned below the first hopper. This will collect the asphalt as it flows out of the first hopper. A feed screw will be positioned below the second hopper providing the ability to reload the hopper #1 with asphalt for further examination by recycling the same asphalt. The feed screw will also be designed with its own inspection equipment which will again analyze the mix ratio as the material is pumped out of hopper #2. The feed screw will provide a constant flow for more accurate analyses of mix ratios. The feed screw will provide a means for removing the test material from the portable test trailer. This is a test of the mix ratio with a controlled flow of asphalt and will provide a solution for monitoring the mix ratio if the free flowing material is not acceptable.

Figure 35:
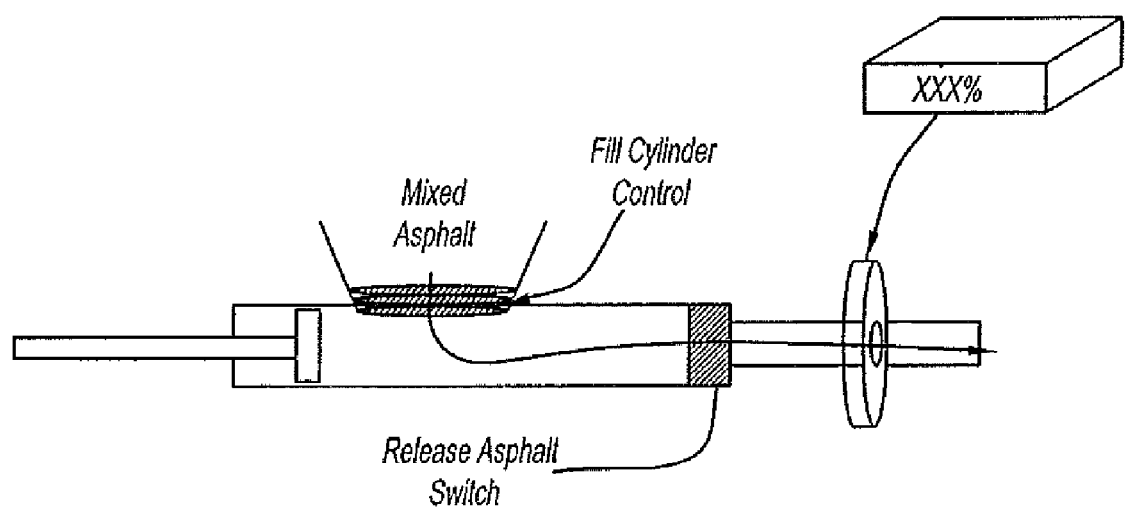
FIG. 35 illustrates an optional piston delivery system with similar results as feed screw.

20. FIG. 35 illustrates an optional piston delivery system with similar results as the feedscrew described above. The cylinder is preferably filled with asphalt. The piston pushed the asphalt out at a constant speed for monitoring the mix ratio. Optionally, the material will freely flow through the piston.

A portable construction vehicle will allow us to perform our test with minimal disturbance to the asphalt facility. This portability provides us with the capability of testing various facilities.

EQUIPMENT: We will need to build a two tier hopper system. Hopper #1 will be located above the hopper #2. Hopper #1 will be designed to collect manufactured asphalt directly from the mixer used at the asphalt manufacture facilities. A control lever will be positioned below the funneled thruway preventing the asphalt to pass through to the second hopper. A MFT sensor will be positioned below the control lever to 100% inspect the mixture as it falls through the sensor. The second hopper will collect the asphalt and funnel the asphalt to a motorized feed-screw. When activated, the material will be delivered through a pipe which will deliver the asphalt back to hopper for retesting or to an external vehicle.

Task #1, #2: Study Free Fall, Tapered Free Fall, Feed Screw Delivery with and without Reducer:

Fill hopper #1 with manufactured asphalt. Monitor the flowing of material as the control lever is opened. Study the average value and standard deviation, observe and record dispense rate. Determine if any fluctuation in readings is caused by the delivery system or are actually variations in mix ratio. Transfer from hopper #2 back to hopper #1 while studying the results of sensor #2 located after the feed screw. Modify the sensor #1 by adding tubing which limits the flow of material due to the smaller diameter. The backup of material may improve the resulting data from sensor #1. Again use the feed screw to reload the hopper #1. Insert a diameter reducer after sensor #2. Study if this improves the repeatability of the data from sensor #2

TASK #3: Redesign the portable equipment for testing the manufacturing of asphalts. Task #2 will provide us with the necessary information on how to manufacturer the portable test station. If sensor #1 provides us with the quality information the second hopper will still be necessary to remove the asphalt. However this may simplify the feed-screw. We will still need to deliver the asphalts at high through puts when this equipment is used at construction sites.

Task #4: Develop software, electronics, and hardware for portable use at construction sites. Sample test the material delivered.

TASK #5: If free flow is repeatable then design a sensor which fits above the vehicle which will 100% inspect the finished mix ratio as it is dumped into a truck. This same sensor can be adopted to fit various mixers, batch mixers as used at the asphalt manufacturing facility. If the free flow is not acceptable then design a sensor which includes the feed screw. Two types of sensors, one that fits on the batch mixer and another that fits on the truck. Software, electronics and hardware will be developed.

TASK #6: Develop electronics, hardware and software that will help test if mixing time or mixing revolutions are adequate. Develop testing procedures which will evaluate the mixer.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A method for monitoring a mixture ratio of a mixed material prepared for installation comprising the steps of:
   a. providing a first material mixed with taggant particles;
   b. providing a second material taggants-free;
   c. mixing the first and second materials together;
   d. providing a first sensor for monitoring the taggant particles in the first material prior to mixing with the second material and generating a first sense signal representing an amount of the taggant particles per unit volume of the first material flowing adjacent the first sensor;
   e. providing a second sensor for monitoring the taggant particles after mixing of the first and second materials and generating a second sense signal representing an amount of the taggant particles per unit volume of the mixture of the first and second materials flowing adjacent the second sensor; and
   f. providing a third sensor for monitoring the taggant particles and generating a third sense signal representing an amount of the taggant particles per unit volume of the mixture flowing adjacent the third sensor after generating the second sense signal and before completion of installation of the mixed material and ensuring a proper mixture of the first and second materials based upon the first and second sense signals and the third sense signal prior to installation of the mixed material.

2. The method of claim 1 wherein at least one of the first and second sensors is an encircling sensor.

3. The method of claim 1 and further comprising a step of notifying an operator that the mixing of the first and second materials is complete.

4. The method of claim 1 and further comprising a step of detecting with the second sensor an off mixture ratio of the first and second materials caused by moisture in the mixed material.

5. The method of claim 1 and further comprising a step of compensating for an elevated temperature when detecting a mixture ratio of the first and second materials by the second sensor.

6. The method of claim 1 wherein the mixed material is one of asphalt and concrete.

7. The method of claim 1 wherein the steps a. through f. are performed at one of a mixing location remote from an installation site for the mixed material, a mixing location adjacent the installation site for the mixed material, and a vehicle installing the mixed material at the installation site.

8. A method for monitoring a mixture ratio of an asphalt paving material prepared for installation comprising the steps of:
   a. providing a first material mixed with taggant particles;
   b. providing a second material taggants-free;
   c. mixing the first and second materials together to form an asphalt paving material;
   d. providing a first sensor for monitoring the taggant particles in the first material prior to mixing with the second material and generating a first sense signal representing an amount of the taggant particles per unit volume of the first material flowing adjacent the first sensor;
   e. providing a second sensor for monitoring the taggant particles after mixing of the first and second materials and generating a second sense signal representing an amount of the taggant particles per unit volume of the mixture of the first and second materials flowing adjacent the second sensor; and
   f. providing a third sensor for monitoring the taggant particles and generating a third sense signal representing an amount of the taggant particles per unit volume of the mixture flowing adjacent the third sensor after generating the second sense signal and before completion of installation of the asphalt paving material and ensuring a proper mixture of the first and second materials based upon the first and second sense signals and the third sense signal prior to installation of the asphalt paving material.

9. The method of claim 8 including performing the step f. to sense at least one of separation of the first and second materials and compaction of the asphalt paving material.

10. The method of claim 8 wherein at least one of the first and second sensors is an encircling sensor.

11. The method of claim 8 and further comprising a step of notifying an operator that the mixing of the first and second materials is complete.

12. The method of claim 8 and further comprising a step of detecting with the second sensor an off mixture ratio of the first and second materials caused by moisture in the asphalt paving material.

13. The method of claim 8 and further comprising a step of compensating for an elevated temperature when detecting a mixture ratio of the first and second materials by-the second sensor.

14. The method of claim 8 wherein the steps a. through f. are performed at one of a mixing location remote from an installation site for the asphalt paving material, a mixing location adjacent the installation site for the asphalt paving material, and a vehicle installing the asphalt paving material at the installation site.

15. An apparatus for monitoring a mixture ratio of a mixed material comprising:
   a first sensor for monitoring the taggant particles in the first material prior to mixing with the second material and generating a first sense signal representing an amount of the taggant particles per unit volume of the first material flowing adjacent the first sensor;
   a second sensor for monitoring the taggant particles after mixing of the first and second materials by generating a second sense signal representing an amount of the taggant particles per unit volume of the mixture of the first and second materials flowing adjacent the second sensor;
   a control device responsive to the first and second sense signals for ensuring a proper mixture of the first and second materials prior to installation of the mixed material; and
   a third sensor for monitoring the taggant particles and generating a third sense signal representing an amount of the taggant particles per unit volume of the mixture flowing adjacent the third sensor after generating the second sense signal and before completion of installation of the mixed material, the control device ensuring a proper mixture of the first and second materials based upon the first, second and third sense signals prior to installation of the mixed material.

16. The apparatus of claim 15 wherein at least one of the first and second sensors is an encircling sensor.

17. The apparatus of claim 15 wherein the control device notifies an operator that the mixing of the first and second materials is complete.

18. The apparatus of claim 15 wherein the control device detects with the second sensor an off mixture ratio of the first and second materials caused by moisture in the mixed material.

19. The apparatus of claim 16 wherein the control device compensates for an elevated temperature when detecting a mixture ratio of the first and second materials by the second sensor.

* * * * *